(12) United States Patent
Lelah et al.

(10) Patent No.: US 7,449,194 B2
(45) Date of Patent: *Nov. 11, 2008

(54) ANTIMICROBIAL BODY COVERING ARTICLES

(75) Inventors: Michael D. Lelah, Arlington Heights, IL (US); Joel J. Kampa, Lakehills, TX (US); Sumner A. Barenberg, Chicago, IL (US)

(73) Assignee: MicroActive Corp., Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/338,923

(22) Filed: Jan. 8, 2003

(65) Prior Publication Data

US 2003/0235605 A1   Dec. 25, 2003

Related U.S. Application Data

(60) Provisional application No. 60/346,591, filed on Jan. 8, 2002.

(51) Int. Cl.
*A01N 25/34* (2006.01)

(52) U.S. Cl. .............................. 424/404; 2/457; 2/901; 424/613; 424/661; 424/663; 424/700; 424/712; 424/718; 523/122

(58) Field of Classification Search .................. 424/402, 424/403, 411, 712, 661, 663, 700, 613, 9.8, 424/10.3, 10.4, 404, 718
See application file for complete search history.

(56) References Cited

U.S. PATENT DOCUMENTS

| | | | |
|---|---|---|---|
| 4,533,691 A | | 8/1985 | Khalil et al. |
| 4,775,585 A | | 10/1988 | Hagiwara et al. |
| 4,878,974 A | | 11/1989 | Kagawa |
| 4,906,464 A | | 3/1990 | Yamamoto et al. |
| 4,911,898 A | | 3/1990 | Hagiwara et al. |
| 4,938,955 A | | 7/1990 | Niira et al. |
| 5,009,898 A | | 4/1991 | Sakuma et al. |
| 5,104,660 A | | 4/1992 | Chvapil et al. |
| 5,296,238 A | | 3/1994 | Sugiura et al. |
| 5,357,636 A | * | 10/1994 | Dresdner et al. ............. 2/161.7 |
| 5,360,609 A | | 11/1994 | Wellinghoff |
| 5,405,664 A | | 4/1995 | Sirinyan et al. |
| 5,407,685 A | | 4/1995 | Malchesky et al. |
| 5,441,717 A | | 8/1995 | Ohsumi et al. |
| 5,474,797 A | | 12/1995 | Sioshansi et al. |
| 5,631,300 A | | 5/1997 | Wellinghoff |
| 5,639,295 A | | 6/1997 | Wellinghoff et al. |
| 5,650,446 A | | 7/1997 | Wellinghoff et al. |
| 5,668,185 A | | 9/1997 | Wellinghoff |
| 5,695,814 A | | 12/1997 | Wellinghoff et al. |
| 5,705,092 A | | 1/1998 | Wellinghoff et al. |
| 5,707,739 A | | 1/1998 | Wellinghoff et al. |
| 5,714,445 A | | 2/1998 | Trinh et al. |
| 5,725,867 A | | 3/1998 | Mixon |
| 5,888,528 A | | 3/1999 | Wellinghoff et al. |
| 5,914,120 A | | 6/1999 | Wellinghoff et al. |
| 5,922,776 A | | 7/1999 | Wellinghoff et al. |
| 5,965,264 A | | 10/1999 | Barenberg et al. |
| 5,980,826 A | | 11/1999 | Barenberg et al. |
| 6,046,243 A | | 4/2000 | Wellinghoff et al. |
| 6,277,408 B1 | | 8/2001 | Wellinghoff et al. |
| 6,361,786 B1 | | 3/2002 | Shanbrom |
| 6,365,278 B1 | | 4/2002 | Hoerner et al. |
| 6,372,333 B1 | | 4/2002 | Sugiyama et al. |
| 6,420,455 B1 | * | 7/2002 | Landgrebe et al. .......... 523/122 |
| 6,436,422 B1 | | 8/2002 | Trogolo et al. |
| 6,488,998 B1 | | 12/2002 | Crook |
| 6,495,158 B1 | | 12/2002 | Buseman et al. |
| 2003/0157150 A1 | | 8/2003 | Lee |

FOREIGN PATENT DOCUMENTS

| | | |
|---|---|---|
| EP | 0 351 636 A2 | 1/1990 |
| JP | 06-098927 | 4/1994 |
| WO | 96/41526 | * 12/1996 |
| WO | 99/39574 | * 8/1999 |
| WO | WO 99/39574 | 8/1999 |
| WO | WO 00/69775 A1 | 11/2000 |

OTHER PUBLICATIONS

International Search Report for PCT/US03/00480 dated Aug. 11, 2003.

* cited by examiner

*Primary Examiner*—Neil Levy
(74) *Attorney, Agent, or Firm*—Senniger Powers

(57) ABSTRACT

A polymeric body covering article that generates and releases gas upon activation by electromagnetic energy and/or moisture. The gas provides antimicrobial and/or antiodor protection to objects in contact or in proximity to the interior surface of the article and/or to objects in contact or in proximity to the exterior surface of the article.

16 Claims, No Drawings

ANTIMICROBIAL BODY COVERING ARTICLES

FIELD OF THE INVENTION

The present invention relates to body covering articles, such as gloves, for retarding, controlling, killing or preventing microbiological contamination (e.g., bacteria, fungi, viruses, mold spores, algae, and protozoa) and/or neutralizing odors.

BACKGROUND OF THE INVENTION

Body covering articles, such as vinyl gloves, are used in a variety of food service, general cleaning, handling, protection, non-medical, medical and hospital applications as a barrier layer to prevent or reduce contamination by microorganisms. Commercially available body covering articles, such as gloves, typically do not contain antimicrobial components or impart any antimicrobial properties. If the gloves contact a contaminated surface, the gloves can transfer the microorganisms to other surfaces contacted by the gloves (i.e., cross contamination).

Antimicrobial treated body coverings are known in the art. For example, U.S. Pat. No. 6,361,786 to Shanbrom describes organic polymer based gloves impregnated by absorption with a disinfectant organic dye. U.S. Pat. No. 6,365,278 to Hoemer et al. describes multilayer materials comprising at least one continuous layer carrying a contact biocide inserted between inert barriers layers. In these antimicrobial products, the microbial contaminant must directly contact the biocide such that surfaces in close proximity to the biocide are not decontaminated. Also, these contact biocides may not control the microbe for hours or days, thus creating a window of vulnerability within which the microbe may be transmitted to unprotected surfaces via cross-contamination.

Triclosan (5-chloro-2-(2,4-dichlorophenoxy)phenol) has been used as a contact biocide. For example, U.S. Pat. No. 6,488,998 B1 to Crook describes a multilayer pipe wrap for preventing microbiologically influenced corrosion in buried conduits. Triclosan is blended into a molten low density polyethylene (LDPE) resin from which an antimicrobial conduit contacting layer is formed. The triclosan layer is then formed into a laminate with a high density polyethylene (HDPE) layer sandwiched between said triclosan layer and a second LPDE layer that forms the outermost, or environment contacting layer. U.S. Pat. No. 6,495,158 B1 to Buseman et al. describes an acne treatment adhesive patch with a polymeric backing and comprising, among other constituents, a topical biocide such as triclosan absorbed into the backing.

A number of metal ions have been shown to possess antibiotic activity including silver, copper, zinc, mercury, tin, lead, bismuth, cadmium, chromium and thallium ions. Antibiotic ceramics have been prepared by replacing all or part of their ion-exchangeable ions with antibiotic metal ions. Suitable ceramics include zeolites, hydroxyapatite, zirconium phosphates. See U.S. Pat. Nos. 5,009,898; 5,296,238; 5,441, 717; 5,405,664; 5,474,797; 4,011,898; 4,938,955; 4,906,464; and 4,775,585. U.S. Pat. No. 6,436,422 to Trogolo et al., which is incorporated by reference herein, discloses the incorporation of antibiotic ceramic particles in a hydrophilic polymer, such as polyurethane. Although the antibiotic polymers are reported as being effective biocides, they must be in intimate contact with the microbial contaminant to be effective.

Chlorine dioxide ($ClO_2$) and sodium chlorite have been used as biocides in food packaging, cosmetics, pharmaceuticals, binder and coatings. Wellinghoff et al. have formulated composites that include a hydrophobic phase containing an acid releasing agent and a hydrophilic phase containing anions which are capable of generating a gas, such as chlorite anions. The composite is substantially free of water until it is exposed to moisture. Once exposed to moisture, acid and hydronium ions are generated in the hydrophobic phase. The hydronium ions migrate to the hydrophilic phase and react with the anions to release the gas from the composite. These composites are composed of and generate only FDA approved substances or substances generally recognized as safe. The composites can be used for food packaging and other applications where the substances can be ingested by, or in contact with humans. These composites are described in U.S. Pat. Nos. 5,650,446, 5,707,739, 5,631,300, 5,668,185, 5,695,814, 5,705,902, 5,888,528, and 6,046,243.

In U.S. Pat. No. 5,360,609, Wellinghoff taught that alkali chlorites could be solubilized in hydrophilic matrices containing amides and/or polyhydroxy compounds and mixed with hydrophobic acid releasing phases containing organic acid anhydrides to form interpenetrating networks that will release chlorine dioxide upon exposure to moisture.

Wellinghoff et al. U.S. Pat. No. 5,914,120 discloses a composite formulated for maximum chlorine dioxide release in which the hydrophilic material contains an alpha-amino ether, alcohol or ester and a chlorite salt formed by reaction of an iminium chlorite and a base. Iminium chlorite is unstable to nucleophilic attack by the chlorite anion. When the iminium chlorite is reacted with a base, however, the more stable alpha-amino ether, alcohol or ester and chlorite salt are formed.

Wellinghoff et al. U.S. Pat. No. 5,639,295 describes a method for maximizing chlorine dioxide release from an amine-containing composite by omitting the chlorite source until the composite is applied to a surface. After application, the composite is exposed to chlorine dioxide gas that either reacts with the amine to form iminium chlorite in situ or dissolves in the amine to provide chlorite anions. The composite is then activated in the presence of moisture to release chlorine dioxide. The composite can be exposed to elevated temperatures during processing, storage and application because the hydrophilic material does not contain iminium chlorite or any chlorite anions that could decompose at such temperatures. The method also precludes premature release of chlorine dioxide from the composite.

Wellinghoff et al. U.S. Pat. No. 6,277,408 describes powders prepared from an acid releasing agent and silicate particles containing anions capable of generating a gas upon exposure to moisture. Alternatively, the powder includes an interpenetrating network containing a solution solution, the anions, and the acid releasing agent. In another embodiment, the powder includes a solid solution containing a water-soluble silicate, the anions and an acid releasing agent.

Wellinghoff et al. U.S. Pat. No. 5,965,264 describes a powder including a core containing a molecular sieve, and a layer containing an acid releading agent on an outer surface of the core. The core is capable of generating and releasing a gas after hydrolysis of the acid releasing agent.

Wellinghoff et al. WO 00/69775 describes a composition including an energy-activated catalyst capable of being activated by electromagnetic energy, and a solid or solids-containing suspension containing anions capable of being oxidized by the activated catalyst or reacted with species generated during activation of the catalyst to generate a gas.

Barenberg et al. U.S. Pat. No. 5,980,826 describes numerous methods of using composites such as those disclosed by Wellinghoff et al. to retard bacterial, fungal, and viral contamination and growth of molds on food, produce, meat, and other materials and to deodorize carpeting and the like.

Khalil et al. U.S. Pat. No. 4,533,691 teaches a microbial growth inhibiting latex composite containing chlorine dioxide or two or more chemical compounds which react upon mixing to generate chlorine dioxide, homopolymers and copolymers of acrylic acid, and an organic acid or a reducing agent. Use of such latexes as coatings and binders is disclosed.

Wellinghoff, in U.S. Pat. No. 5,922,776 discloses compositions containing an acid releasing polymer, a hydrophilic material and chlorite anions. The composition is optically transparent or translucent and is capable of releasing chlorine dioxide upon hydrolysis of the acid releasing polymer.

There is a need for biocidal articles which perform the same functions as conventional articles while also retarding, controlling, killing or preventing microbiological contamination of the skin or other surfaces and/or controlling odors while also controlling cross contamination. There is also a need for a decontamination method that does not require direct contact of the microbe with the article but rather provides an antimicrobial microatmosphere surrounding the article. There is also a need for such articles that are not susceptible to resistance to the anti-microbial, and that reduce microbial contamination in seconds or minutes to effectively inhibit cross-contamination.

SUMMARY OF THE INVENTION

Among the several features of the invention, therefore, may be noted the provision of a body covering article which retards, controls, kills or prevents microbiological contamination of the skin; the provision of a body covering article which retards, controls, kills or prevents microbiological contamination of a surface in contact or proximal to the article; the provision of a body covering article which minimizes or prevents cross contamination of surfaces in contact with the article after the article has contacted a contaminated surface; and the provision of a body covering article which deodorizes the skin or a surface in contact or in close proximity to the article.

The present invention is directed to a body covering article for controlling microbiological contamination and/or odor, which includes a covering for a portion of a mammalian body. The covering includes a gas-generating composition which is capable of generating and releasing at least one gas upon exposure to light and/or humidity.

Another embodiment of the invention is directed to a body covering article which includes a covering for a portion of a mammalian body wherein the covering, when exposed to light and/or moisture, is capable of controlling odor and/or microbiological contamination on the portion of the body and controlling odor and/or contamination of a surface in contact with the article.

The present invention is also directed to a body covering article for controlling microbiological contamination and/or odor which includes a covering for a device in contact with the mammalian body. The covering includes a gas-generating composition which is capable of generating and releasing at least one gas upon exposure to light and/or humidity. The device is a telephone, bedding, door knob, steering wheel, food handling equipment handles, toilet seat, or bed railing.

Yet another embodiment of the invention is directed to a body covering article for controlling microbiological contamination and/or odor which includes a covering for a device in contact with the mammalian body. The covering includes a gas-generating composition which is capable of generating and releasing at least one gas upon exposure to light and/or humidity, and a colorant capable of changing color when oxidized by the gas.

Another embodiment of the invention is directed to a body covering article for controlling microbiological contamination and/or odor which includes a covering for a device in contact with the mammalian body. The covering includes a gas-generating composition which is capable of generating and releasing at least one gas upon exposure to light and/or humidity. The contamination and/or odor is controlled on an interior surface of the article in contact with the device and on an exterior surface of the article in contact with the body.

The invention is also directed to a process for the preparation of a body covering article by admixing vinyl resin, a plasticizer and a composition containing anions which are capable of generating and releasing at least one gas upon exposure to light and/or humidity to form an admixture, and forming the body covering article from the admixture. The article is capable of generating and releasing at least one gas upon exposure to light and/or humidity.

Another aspect of the invention is directed to a method of using a gas-releasing body covering article by providing a body covering article containing a composition containing anions which are capable of generating and releasing at least one gas upon exposure to light and/or humidity and a colorant capable of changing color when oxidized by the gas, exposing the body covering article to light and/or humidity to generate the gas, and monitoring the color change of the colorant as an indicator of gas-releasing activity.

DESCRIPTION OF THE PREFERRED EMBODIMENTS

In accordance with the present invention, body covering articles, such as gloves, have been made which are capable of generating and releasing a gas which provides antimicrobial and/or antiodor protection on the skin as well as on other surfaces, even without direct surface contact. A composition which generates and releases at least one gas is incorporated into the article itself or applied to a surface of the article to provide such protection. The gas is a microbial agent or deodorant that is fast acting and not susceptible to being rendered ineffective through microbe resistance.

In one embodiment, the body covering article of the invention comprises a covering and a gas-generating composition. The covering of the present invention can be any conventional body covering, such as a glove, cap, apron, or shoe cover, or a device which contacts a part of the body. The covering is comprised of any conventional polymer material such as, for example, polyolefins (e.g., chlorinated polyethylene, polyethylene), polyvinyl chloride, natural and synthetic latex, nitrile, mylar, polyurethane, neoprene or other polymers and materials well known in the art, including combinations of such polymers (e.g., multilayer films including various polymer layers).

The article is treated or prepared so as to incorporate a composition capable of generating and releasing a gas which provides antimicrobial and/or antiodor protection on the skin or other surfaces. The gas-generating composition can be any composition which generates and releases a gas upon exposure to light and/or humidity. Preferably, the composition contains anions capable of being oxidized or reacted to form a gas.

In one embodiment, the composition, when exposed to electromagnetic energy, is capable of generating and releasing at least one gas after activation of an energy-activated catalyst and oxidation or reaction of anions. The composition comprises the catalyst and a solid or a solids-containing suspension which contains the anions that are capable of being oxidized or reacted to generate the gas. Preferably, the composition is an inorganic light activated composition (e.g., Microlite® powder) as described in copending U.S. patent application Ser. No. 09/448,927 and WO 00/69775, all of which are incorporated by reference.

In another embodiment, the composition, when exposed to moisture, is capable of generating and releasing at least one gas after generation of acid and hydronium ions in a hydrophobic material. The hydronium ions migrate to a hydrophilic material within the composition and react with anions to generate and release a gas from the composition. Preferably, the composition is an inorganic moisture activated composition (e.g., Microsphère® powder) as described in copending U.S. patent application Ser. No. 09/138,219, WO 99/39574, and U.S. Pat. Nos. 5,965,264 and 6,277,408, or an organic moisture activated composition as described in U.S. Pat. Nos. 5,360,609, 5,631,300, 5,639,295, 5,650,446, 5,668,185, 5,695,814, 5,705,092, 5,707,739, 5,888,528, 5,914,120, 5,922,776, 5,980,826, and 6,046,243, all of which are incorporated by reference.

Gases with antimicrobial properties that can be generated from the gas-generating compositions include chlorine dioxide, chlorine, sulfur dioxide, carbon dioxide, hydrogen peroxide, and nitrous oxide. Gases with odor neutralizing properties that can be generated from the gas-generating compositions include chlorine dioxide, chlorine, hydrogen peroxide and sulfur dioxide. The anions used to form these gases are provided by salts of the anions and a counterion, such as salts of a chlorite, bisulfite, bicarbonate, hypochlorite, peroxide or nitrite. Chlorite salts are more preferred and form chlorine dioxide. Such gas-generating compositions are described in greater detail below in the section entitled "Gas Generating Compositions."

In a preferred embodiment of the invention, vinyl body covering articles are prepared. The vinyl body covering article is comprised of about 0.5-20 wt. % gas-generating composition, about 0.01-3 wt. % dispersing agent, about 0.005-3.0 wt. % thixotropic agent, and about 74-99 wt. % plastisol. Preferably, the vinyl article comprises about 5.0-8.0 wt. % gas-generating composition, about 0.1-0.3 wt. % dispersing agent, about 0.02-0.1 wt. % thixotropic agent, and about 91-94 wt. % plastisol.

Plastisol is a dispersion of finely divided vinyl resin in a plasticizer. Preferably, the plastisol for use in the invention comprises from about 20 to about 70 wt. % vinyl resin, from about 20 to about 77 wt. % plasticizer, from 0 to about 5.0 wt. % dispersing agent, from 0 to about 5 wt. % stabilizer, and from 0 to about 5 wt. % colorant. Polyvinyl chloride (PVC) is the preferred polymer in the plastisol component. Any suitable plasticizer(s), dispersing agent(s) (surfactant), thixotropic agent(s), stabilizer(s) or colorant(s) known in the art may be used in the plastisol. Preferably, the plasticizer comprises bis(2-ethylhexyl)phthalate (DOP), 2,2,4-trimethyl-1,3-pentanediol diisobutyrate (TXIB), and/or diisononylphthalate (DINP). Preferred surfactants include epoxidized soybean oil or Disperplast® 1150 (a polar acidic ester of a long chain alcohol available from BYK-Chemie of Wesel, Germany). A preferred thixotropic agent is Disperplast® BKY-410 (a modified urea solution available from BYK-Chemie of Wesel, Germany). An example of a suitable stabilizer is a calcium-zinc stabilizer. Any colorant known in the art that provides the desired color, for example blue, yellow, red, etc., may be used. Pigments are more preferred. In the case of chlorine dioxide, the color of some pigments is not affected by its generation and release and significant color change will not occur. Advantageously, some pigments known in the art can be oxidized by chlorine dioxide with a resultant color change, for example from blue to green, and can be used to indicate the activity of the body covering during and after use.

In another preferred embodiment of the invention, body covering articles are made from heat processable polymers such as polyolefins (e.g., polyethylene, chlorinated polyethylene or polypropylene); polyurethane; natural and synthetic latex; nitrile; or neoprene. Such body covering articles are comprised of from about 1 to about 50 wt. % gas generating composition, and from about 50 to about 99 wt. % heat processable polymer(s). For example, a preferred body covering article comprises from about 1 to about 20 wt. % of an energy-activated gas generating composition such as Microlite® powder and from about 80 to about 99 wt. % heat processable polymer such as polyethylene. More preferably, the body covering article comprises from about 2 to about 10 wt. % of an energy-activated gas generating composition such as Microlite® powder and from about 90 to about 98 wt. % heat processable polymer such as polyethylene. In another preferred embodiment, a body covering article comprises from about 10 to about 50 wt. % of a moisture-activated gas generating composition such as Microsphère® powder and from about 50 to about 90 wt. % heat processable polymer such as polyethylene. More preferably, the body covering article comprises from about 10 to about 30 wt. % of an energy-activated gas generating composition such as Microsphère® powder and from about 70 to about 90 wt. % heat processable polymer such as polyethylene.

Conventional film forming additives can be added to the compositions used to make the articles of the invention as needed. Such additives include crosslinking agents, stabilizers (e.g., UV stabilizers), flame retardants, emulsifiers, compatibilizers, lubricants, antioxidants, and colorants. The body covering articles can also include any contact biocide for providing additional antimicrobial protection, such as an antibiotic ceramic, triclosan (a heterocyclic organic antimicrobial compound), silver ions or other antimicrobial metal ions, or isothiocyanate derivatives such as allyl isothiocyanate. Such compositions provide a long-acting direct contact biocide in combination with the generated gas which provides both direct and indirect contact protection. Moreover, such compositions provide contact biocidal protection even in low light or low humidity environments, or can provide extended biocidal protection even after the generated gas is exhausted. Such contact biocides can be incorporated into articles of the invention in the same manner described herein for incorporating the gas generating composition.

The body covering articles of the invention, such as gloves, can be a monolayer (i.e., made of a single layer which emits a gas from both inner and outer surfaces) or a multilayer (i.e., made of more than one layer of which at least one layer emits a gas from at least one of its surfaces). The gas generating composition can be incorporated in one or more of the layers of the multilayer article.

Barrier layers can be incorporated in the inner or outer layer of a multilayer article to provide directionality for the migration of the gas through and out of the article. A gas-generating multilayer body covering article including a barrier layer can be formed from a combination of any of the embodiments. Such an article includes at least one gas generating layer and at least one barrier layer. The gas generating layer includes either an energy-activated catalyst capable of being activated by electromagnetic energy and anions capable of being oxidized or reacted to generate a gas, or a moisture-activated composition including anions capable of reacting with hydronium ions to generate a gas. The barrier layer is adjacent to a surface of the gas generating layer. The barrier layer is transparent to electromagnetic energy, or permeable or semipermeable to moisture such that it transmits the energy or hydronium ions to the gas generating layer. However the barrier layer is impermeable or only semipermeable to the gases generated and released by the gas generating layer. The gas generating layer, when exposed to electromagnetic energy or moisture is capable of generating and releasing the gas after activation of the catalyst or release of hydronium ions in response to moisture, and oxidation or reaction of the anions.

The coverings of the present invention include any clothing for covering a part of the body, such as a glove, apron, gown, bodysuit, trousers, shirt, cap, foot cover, bootie, sock, shoe cover, arm cover, leg cover, incontinence pad or garment, diaper, hair cover, beard cover, face mask, lab coat, condom, body bag or other garment. Such articles also include polyvinyl chloride, natural or synthetic latex, low or high density polyethylene, flourine-based, nylon, polyurethane, polyvinylalcohol, polyvinylidine fluoride, polyamide, polyacrylonitirile poly(sytrene-butadiene-styrene) or nitrile gloves as used in food service, food processing, security, general cleaning, handling, protection, non-medical, medical and hospital applications. The gloves can be either powdered (e.g., with corn starch powder on the interior), or powder-free (e.g., with a layer of polyurethane on the inner surface of the glove to provide easy wearing characteristics). The gloves can be non-colored or colored (e.g., blue) and of various sizes (XS, S, M, L, XL, etc). The articles of the present invention can also be devices that contact a part of the body, such as a telephone cover, door knob cover, toilet seat cover, bedding, transportation seating, computer cover, manually operated equipment handle cover, bed railing cover, biohazard container or laundry container.

The articles of the invention will perform the same functions as other commercial body coverings, with the added advantage of providing a level of antimicrobial and/or anti-odor protection. The articles of the invention can be used to prevent or reduce contamination or cross contamination of foods, and protect foods for food handling, food processing, and food service. The body coverings can also be used to protect personnel and decontaminate articles from ambient organisms and from bioterrorist organisms such as anthrax, smallpox, ebola, HIV, etc. For example, the body coverings can be used in mail and package handling, and in security for the handling of suspect articles and personnel. The body coverings can also be used to provide antimicrobial protection to medical personnel such as dentists, doctors, medical examiners, nurses, emergency medical technicians, and orderlies.

Manufacture of Body Covering Articles

The gas-generating composition can be incorporated into the articles of the invention by various means. The composition can be mixed with other materials used in making the article so that the composition is distributed throughout the article. For example, the gas-generating composition can be mixed with a polymer to form a mixture from which the article is directly formed as in Examples 1 and 2. Alternatively, the gas-generating composition may be compounded and pelletized with a polymeric material via conventional means to form pellets. Optionally, the pellets can be mixed with other ingredients such as, for example polymers, plasticizers, dispersants and the like to be used in the conventional forming or molding processes. For example, the polymer material and a gas-generating powder or pellets can be mixed together in a mixer, such as a Henschel mixer, and fed to an extruder or molding apparatus operated at a temperature not exceeding about 200° C. to form a melt. The melt can be cast-extruded as a sheet such as a film, formed into pellets using dry air cooling on a vibrating conveyer, or formed into a desired shape by conventional injection-molding, thermal-forming, spun-bonded, nonwovens, spray coatings or compression-molding methods. An article can also be coated with the gas-generating composition by dip coating the article in a liquid gas-generating composition which dries to form a film on at least one surface of the article. Alternatively, the gas-generating composition can be incorporated in a coating that is applied to at least one surface of the article (e.g., in a polyurethane coating which lines the interior of a glove). The gas-generating composition can also be a powder which is mixed with a powder to be applied to at least one surface of the article (e.g., mixed with corn starch as conventionally used to make powdered gloves).

In one embodiment, vinyl body covering articles are prepared from a mixture comprising gas-releasing particles admixed with a vinyl polymer, and optional other components such as plasticizers, dispersants, surfactants, stabilizers and pigments. The vinyl polymer is preferably in the form of a plastisol. The body covering articles may be prepared by dip and extrusion methods known in the art. In the case of gloves, dip processing is preferred. In a preferred embodiment, a vinyl article is prepared by adding the dispersing agent to the vinyl plastisol, then adding the gas generating composition, colorant (if any), surfactant, and finally the thixotropic agent, with stirring, followed by deaeration and processing as for standard vinyl gloves, however under darkened conditions. Gloves are produced and packaged under dark or low light conditions (i.e., less than about three ft candles), and are packaged in dispenser boxes, or other suitable packaging. The components may be added in any order to the blend however it is generally preferred to add the thixotropic agent after the gas-releasing composition and any colorant have been adequately dispersed.

The gas-releasing compositions for use in the articles of the invention are preferably energy or moisture activated. If energy activated compositions are used in the production line, which includes material staging areas, mixing tanks, storage tanks, dip tanks, forming stations, etc., as well as the packaging lines, that equipment should be protected from strong light in order to inhibit premature gas release which may compromise finished product integrity. Generally this may be accomplished by using covered processing vessels, shielding the manufacturing and packaging areas from sunlight and artificial light and/or the use of low lighting or indirect lighting.

Preferably, the gas releasing compositions include anions that are oxidized or reacted to form the gas, such as chlorite. Preferred forms of chlorite include energy-activated Microlite® powder, moisture-activated Microsphère® powder and a silicate-chlorite solid solution (as disclosed, for example in U.S. Pat. No. 6,277,408 to Wellinghoff). Silicate-chlorite solutions are preferred because the chlorite content is much greater at the same inorganic solid loading such that more chlorine dioxide is available for generation and release. Also, such solid solutions can be processed at relatively high temperature. In some applications, micronized sodium chlorite based compositions are preferred over solubilized or nano-particle sodium chlorite compositions because the low surface to volume ratio of the chlorite particulate retards reaction with the hydrophobic acid releasing groups during melt processing. However, depending upon the application, the benefits of larger particle size chlorite must be balanced against the physical characteristics such as strength, elongation, elasticity and feel that result from the incorporation of the large particles.

The gas-releasing particles (powder) should be incorporated into the vinyl plastisol with agitation in vessels that preferably include baffling. Moreover, agitation means such as impellers that provide efficient mixing (as by, for example, pumping or shear action) but that minimize air entrapment are preferred. Moreover, agitation should be employed throughout processing to assure that powder sedimentation is minimized. By maximizing mixing efficiency, adequate powder break-up and dispersion produces a homogeneous plastisol-powder suspension with resultant high quality finished product that meets both gas-release and mechanical property requirements. In addition to mixing the suspension, storage, mixing, and dip tank filtration systems should be used to remove undispersed or undissolved components that would otherwise adversely affect product quality from the dip mixture. Any conventional filtration means which selectively removes the undispersed powder, undissolved plastisol, or other undissolved components from solution, such as filter presses and filter cartridges, may be used.

In another embodiment the body covering articles are prepared from a melt, emulsion or mixture comprising gas-releasing particles admixed with a heat processable polymer including: polyolefins such as polyethylene, chlorinated polyethylene or polypropylene; polyurethane; natural and synthetic latex; nitrile; neoprene; or other polymers and materials well known in the art.

In this embodiment the gas-releasing composition can be incorporated into the polymer in various ways. In a direct route, the gas generating composition (e.g., a chlorite source such as Microlite® powder or Microsphère® powder) is blended with a polymer resin or a combination of polymer resins in pellet or powder form. Preferably the resin is powdered. Sheets (such as films, nonwovens, wovens) or other polymer based materials may be directly formed from this blend by blow molding, film casting, spun fiber, or other conventional polymer processing methods known in the art. From these formed materials, body covering articles can be formed by conventional operations such as heat sealing, cutting, sewing, etc.

In an indirect route, the gas generating composition (e.g., a chlorite source such as Microlite® powder or Microsphère® powder) is blended with a polymer resin or a combination of polymer resins in pellet or powder form. From that blend, a masterbatch is extruded. The masterbatch is then used to blow or cast sheets or films, spin fibers, or to produce sheets (such as films, non-wovens or wovens) or other polymer based materials by conventional polymer processing methods well known in the art. Body covering articles are then made from these formed materials by conventional operations such a heat sealing, cutting, sewing, etc.

Sheets, body covering articles or other objects formed from the composition of the present invention may be produced by a variety of standard procedures known in the art. For example, in dip coating processes, a mixture is formed in a compounding step. The gas releasing composition may be pre-incorporated into the polymers from which the mixture is formed such as, for example, granular blends, resins, polymers and plastics. Alternatively, the gas generating composition may be added directly to the mixture from which the finished article is prepared as in Examples 1, 2, 7 and 8. In this case the gas generating composition is preferably finely powdered. Optionally, stabilizers, plasticizers, surfactants, humectants or desiccants may be added. Preferred stabilizers include alkali hydroxide. Based on experimental evidence to date, if the gas generating composition includes an anion source such as sodium chlorite, a mixture temperature in excess of about 160° C. for an extended period of time is generally not preferred. However, vinyl gloves of the present invention (i.e. comprising sodium chlorite) are typically processed at temperatures as high as about 240° C. for times not to exceed about 30 minutes, and more preferably less than about 20 minutes. Where melt temperatures in excess of about 160° C. for an extended period of time is required it is preferred that the anions of the gas releasing component are stabilized through dissolution in an amorphous, paracrystalline or crystalline phase as described in more detail below. Typically, a form (mold) is heated and dipped into the mixture, removed and drained to the desired film thickness, and heated in an oven to fuse (or vulcanize, cure, cross-link, etc.) the materials and form the finished article. This procedure is typically used for forming gloves.

If multilayer articles are to be formed, the above processes may be repeated the number of times corresponding to the number of additional layers desired. For example, the gas-generating composition can be incorporated in a coating that is applied to at least one surface of the article (e.g., in a polyurethane coating which lines the interior of a glove). Alternatively, gas-releasing layers comprised of the same and/or different polymer can be successively applied or sandwiched between non gas-releasing layers. In one embodiment, a powdered gas-releasing composition may be sandwiched between gas-releasing and/or non gas-releasing layers to provide a particularly high anion loading. In high speed manufacturing processes, or where the composition of the layers differs, additional dip tanks are typically required. For efficient manufacture, the steps should occur in rapid succession with the time for each step minimized. Once the final layer is formed, the former is cooled, a cuff can be formed on the article if it is a glove, and the article is stripped from the former and collected for packaging.

In extrusion molding, preformed pellets or a polymer melt comprised of a composition of the present invention is fed through a heating element to raise the temperature above $T_g$, and the resulting plasticized polymer is then forced through a die to create an object of desired shape and size. Optionally however, a gas can be blown through the die of the extruder to form sheets, films or body coverings from the plasticized polymer. Injection molding involves heating preformed pellets or a polymer melt comprised of a composition of the present invention above $T_g$, and in some cases above $T_m$, pressurized transferring to a mold, and cooling the formed polymer in the mold to a temperature below $T_g$. In compression molding, solid polymer is placed in a mold section, the mold chamber is sealed with the other section, pressure and heat are applied, and the softened polymer flows to fill the mold. The formed polymer object is then cooled and removed from the mold. Finally, blow molding entails extrusion of a plasticized polymer tube into a mold and blowing up the tube to fill the mold.

For purposes of this invention, the glass transition temperature ($T_g$) is defined as the lowest temperature at which a polymer can be considered softened and flowable. ($T_m$) is the temperature at which the structure of a crystalline polymer is destroyed to yield a liquid.

In another forming process, gas-releasing fibers can be spun from a melt comprising a polymer and a gas-releasing composition. Fiber spinning is well known in the art and fiber spinning equipment is commercially available. The as-spun fibers may be drawn, or elongated, during the spinning process step to produce a fine diameter fiber of predetermined thickness. Additionally or alternatively, the as spun fibers can be drawn in a second step at a temperature whereby the polymer is sufficiently elastic to allow elongation without breakage. This temperature is usually below the $T_g$ and in some cases may be below the $T_m$. Gas-releasing spun fibers may then be further processed into woven articles or may be used as fibers for attachment means such as sewing, suturing, banding and the like.

In addition to formation of sheets or body covering articles in melt extrusion, dip coat and spinning processes, the melt processable compositions can be applied as a film by using well known procedures such as hot melt, spray coat, spin casting, knife casting, float casting, curtain coat, dry wax, wet wax, coextrusion and lamination processes. Moreover, multilayer gas-releasing body covering articles may be prepared by any combination of processes including melt extrusion, dip coat, spinning and film coating.

Advantageously, sheets (such as films), made from the organic moisture activated compositions (as described below and in U.S. Pat. No. 5,705,092) can be used to form body covering articles of the invention without the inclusion of a polymer component other than those described for making the films. The composite can be formulated as an extrudate, as separate layers of hydrophilic or hydrophobic materials or be applied as a film by using well known hot melt, dip coat, spray coat, curtain coat, dry wax, wet wax, and lamination processes.

In an alternate embodiment, the inner surface of a standard, non gas-releasing body covering article, such as a glove produced by any means known in the art or a gas-generating glove formed from any embodiment or combination of embodiments of the present invention, can be provided with a polyurethane layer containing Microlite® powder or Microsphère® powder to give a gas-releasing powder-free article with easy slip-on characteristics. Microlite® powder or Microsphère® powder is suspended in polyurethane to a loading of about 5 wt % to about 50 wt %, and more preferably about 10 wt % to about 40 wt %. The polyurethane is then applied as a thin coating to the outer surface of the article before it is removed from the form. Preferably the coating thickness is less than about 10 mil (0.025 cm) and more preferably less than about 5 mil (0.013 cm). After coating, the article may be removed from the form whereupon it is inverted resulting in the polyurethane coating being on the interior surface of the article.

In another alternate embodiment of the invention, standard, non gas-releasing gloves (produced by any means known in the art) or a gas-generating glove formed from any embodiment or combination of embodiments of the present invention can comprise a lubricant(s) to facilitate user fitting. Examples of lubricants include corn starch, silica, sand, or antiblock and antislip agents known in the art. The lubricant generally imparts a soft, silky, satiny, easy fit, comfort or feel property to the glove. In one embodiment, a lubricant is added by tumbling the preformed gloves in a powdered lubricant or by spraying, brushing or wiping a lubricant slurry or solution onto a preformed gloved. Gloves prepared in this manner are known commercially as powdered or prepowdered gloves. Hydrolyzed corn starch is a preferred lubricant. Microsphère® powder or Microlite® powder in a preferred ratio of about 1% to about 25% by weight based on the lubricant can be admixed with the lubricant to create an antimicrobial powder inner covering for slip-on ease with antimicrobial effects. In another embodiment, lubricant powders, including Microsphère® powder, Microlite® powder, silica or sand may be added to the vinyl plastisol mixture whereby they are embedded in the vinyl article to produce the desired comfort or feel property to the glove.

Gas Generating Compositions

The gas-releasing composition is typically one which generates and releases a gas upon exposure to energy and/or humidity. In a first embodiment controlled sustained release of a gas such as chlorine dioxide can be generated from a composition containing an energy-activated catalyst and anions when the composition is exposed to electromagnetic energy such as visible or ultraviolet light. Energy activated gas-generating compositions are described in U.S. patent application Ser. No. 09/448,927 and WO 00/69775, and are commercially available under the Microlite® trademark (Bernard Technologies). The anions are either oxidized by the activated catalyst or reacted with species generated during activation of the catalyst to generate the gas. The generation of gas can be suspended by stopping exposure of the composition to electromagnetic energy, and resumed by again exposing the composition to electromagnetic energy. The composition can be repeatedly activated and deactivated in this manner as needed for a desired use. Unlike moisture-activated materials that generate hydronium ions, the energy-activated composition can be processed at high pH preventing decomposition of the anions used to generate the gas. The composition preferably includes a photoactive catalyst so that the anions are photo-oxidized. The composition can also be composed entirely of inorganic materials so that it is odorless.

The gas-releasing composition preferably comprises between about 50 wt. % and about 99.99 wt. % of an energy-activated catalyst capable of being activated by electromagnetic energy, and between about 0.01 wt. % and about 50 wt. % of a source of anions capable of being oxidized by the activated catalyst or reacted with species generated during activation of the catalyst to generate a gas, and more preferably, between about 80 wt. % and about 98 wt. % of the energy-activated catalyst and between about 2 wt. % and about 20 wt. % of the anion source, and most preferably, between about 86 wt. % and about 96 wt. % of the energy-activated catalyst and between about 4 wt. % and about 14 wt. % of the anion source. When the composition is exposed to electromagnetic energy, the energy-activated catalyst is activated and the anions are oxidized or reacted to generate and release the gas.

Without being bound by a particular theory of the invention, it is believed that the energy activated composition generates a gas via one or more of the following mechanisms. When exposed to electromagnetic energy, the energy-activated catalyst absorbs a photon having energy in excess of the band gap. An electron is promoted from the valence band to the conduction band, producing a valence band hole. The valence band hole and electron diffuse to the surface of the energy-activated catalyst where each can chemically react. An anion is oxidized by the activated catalyst surface when an electron is transferred from the anion to a valence band hole, forming the gas. It is believed that chlorine dioxide or nitrogen dioxide are generated by such transfer of an electron from a chlorite or nitrite anion to a valance band hole. It is believed that these and other gases, such as ozone, chlorine, carbon dioxide, nitric oxide, sulfur dioxide, nitrous oxide, hydrogen sulfide, hydrocyanic acid, and dichlorine monoxide, can also be formed via reaction of an anion with protic species generated during activation of the catalyst by abstraction of an electron from water, chemisorbed hydroxyl, or some other hydrated species. The gas diffuses out of the composition into the surrounding atmosphere for a period of up to about six months to affect materials situated near the composition. Compositions that release several parts per million of gas per cubic centimeter per day for a period of at least one day, one week, one month or six months can be formulated by the processes of the present invention for a variety of end uses, including deodorization, freshness enhancement, control, delay or prevention of chemotaxis such as reduction or inhibition of insect infestation, control, reduction, inhibition or prevention of biochemical decomposition, respiration control, and control, delay, destruction or prevention of the growth of microorganisms such as bacteria, molds, fungi, algae, protozoa, and viruses on materials. Although the compositions generally provide controlled sustained release of a gas, the compositions can be formulated so that gas is released during less than one day if desired for a particular end use.

Any source containing anions that are capable of being oxidized by the activated catalyst or reacted with species generated during excitation of the catalyst to generate a gas can be used in the composition. An anion is capable of being oxidized by the activated catalyst to generate a gas if its oxidation potential is such that it will transfer an electron to a valence band hole of the energy-activated catalyst. Preferably, a solid contains the anions. Suitable solids include a salt of the anion and a counterion; an inert material such as a sulfate, a zeolite, or a clay impregnated with the anions; a polyelectrolyte such as polyethylene glycol, an ethylene oxide copolymer, or a surfactant; a solid electrolyte or ionomer such as nylon or Nafion™ (DuPont); or a solid solution. When the composition is a solids-containing suspension, a salt dissociates in a solvent to form a solution including anions and counterions, and the energy-activated catalyst is suspended in the solution. A powder can be formed, for example, by drying this suspension or by physically blending the solid (e.g., salt particles) with the energy-activated catalyst particles.

Suitable salts for use as the anion source include an alkali metal chlorite, an alkaline-earth metal chlorite, a chlorite salt of a transition metal ion, a protonated primary, secondary or tertiary amine, or a quaternary amine, an alkali metal bisulfite, an alkaline-earth metal bisulfite, a bisulfite salt of a transition metal ion, a protonated primary, secondary or tertiary amine, or a quaternary amine, an alkali metal sulfite, an alkaline-earth metal sulfite, a sulfite salt of a transition metal ion, a protonated primary, secondary or tertiary amine, or a quaternary amine, an alkali metal sulfide, an alkaline-earth metal sulfide, a sulfide salt of a transition metal ion, a protonated primary, secondary or tertiary amine, or a quaternary amine, an alkali metal bicarbonate, an alkaline-earth metal bicarbonate, a bicarbonate salt of a transition metal ion, a protonated primary, secondary or tertiary amine, or a quaternary amine, an alkali metal carbonate, an alkaline-earth metal carbonate, a carbonate salt of a transition metal ion, a protonated primary, secondary or tertiary amine, or a quaternary amine, an alkali metal hydrosulfide, an alkaline-earth metal hydrosulfide, a hydrosulfide salt of a transition metal ion, a protonated primary, secondary or tertiary amine, or a quaternary amine, an alkali metal nitrite, an alkaline-earth metal nitrite, a nitrite salt of a transition metal ion, a protonated primary, secondary or tertiary amine, or a quaternary amine, an alkali metal hypochlorite, an alkaline-earth metal hypochlorite, a hypochlorite salt of a transition metal ion, a protonated primary, secondary or tertiary amine, or a quaternary amine, an alkali metal cyanide, an alkaline-earth metal cyanide, a cyanide salt of a transition metal ion, a protonated primary, secondary or tertiary amine, or a quaternary amine, an alkali metal peroxide, an alkaline-earth metal peroxide, or a peroxide salt of a transition metal ion, a protonated primary, secondary or tertiary amine, or a quaternary amine. Preferred salts include sodium, potassium, calcium, lithium or ammonium salts of a chlorite, bisulfite, sulfite, sulfide, hydrosulfide, bicarbonate, carbonate, hypochlorite, nitrite, cyanide or peroxide. Commercially available forms of chlorite and other salts suitable for use, can contain additional salts and additives such as tin compounds to catalyze conversion to a gas.

The gas released by the composition will depend upon the anions that are oxidized or reacted. Any gas formed by the loss of an electron from an anion, by reaction of an anion with electromagnetic energy-generated protic species, by reduction of a cation in an oxidation/reduction reaction, or by reaction of an anion with a chemisorbed molecular oxygen, oxide or hydroxyl radical can be generated and released by the composition. The gas is preferably chlorine dioxide, sulfur dioxide, nitrous oxide, carbon dioxide, dichlorine monoxide, chlorine or ozone.

Chlorine dioxide gas is generated and released if the composition contains a source of chlorite anions. Suitable chlorite sources that can be incorporated into the composition include alkali metal chlorites such as sodium chlorite or potassium chlorite, alkaline-earth metal chlorites such as calcium chlorite, or chlorite salts of a transition metal ion, a protonated primary, secondary or tertiary amine, or a quaternary amine such as ammonium chlorite, trialkylammonium chlorite, and quaternary ammonium chlorite. Suitable chlorite sources, such as sodium chlorite, are stable at processing temperatures in excess of about 90° C. when incorporated in the compositions of the present invention, allowing for processing at relatively high temperatures. Chlorine dioxide-releasing compositions can be used to deodorize, enhance freshness, retard, prevent, inhibit, or control chemotaxis, retard, prevent, inhibit, or control biochemical decomposition, retard, prevent or control biological contamination (e.g., deactivate biological contaminants following biological warfare), or to kill, retard, control or prevent the growth of bacteria, molds, fungi, algae, protozoa, and viruses.

Sulfur dioxide is generated and released if the composition contains bisulfite or sulfite anions. Bisulfite sources that can be incorporated into the composition include alkali metal bisulfites such as sodium bisulfite or potassium bisulfite, alkaline-earth metal bisulfites such as calcium bisulfite, or bisulfite salts of a transition metal ion, a protonated primary, secondary or tertiary amine, or a quaternary amine. Such bisulfite salts dissociate in solution to form bisulfite anions and possibly sulfite anions. Sulfur dioxide gas-releasing compositions can be used for food preservation (e.g. to inhibit biochemical decomposition such as browning of produce), disinfection, and inhibition of enzyme-catalyzed reactions. The compositions can also be used for reduction of chlorine gas concentration in catalytic cycles where aluminum or iron powder is used to selectively scrub chlorine from a mixture of chlorine and chlorine dioxide. The compositions are also useful in modified atmosphere packaging by placing the composition within a package, exposing the composition to electromagnetic energy to generate sulfur dioxide, and sealing the package to create a sulfur dioxide atmosphere within the package.

Chlorine gas and dichlorine monoxide are generated and released from a composition containing hypochlorite anions. Acceptable sources of hypochlorite anions include alkali metal hypochlorites such as sodium hypochlorite, alkaline-earth metal hypochlorites such as calcium hypochlorite, or hypochlorite salts of a transition metal ion, a protonated primary, secondary or tertiary amine, or a quaternary amine. Chlorine gas-releasing compositions can be used in processing meat, fish and produce and as an insecticide. Dichlorine monoxide releasing compositions can be used as a biocide.

Carbon dioxide gas is generated and released if a composition contains a source of bicarbonate or carbonate anions.

Suitable bicarbonate sources that can be incorporated into the composition include alkali metal bicarbonates such as sodium bicarbonate, potassium bicarbonate, or lithium bicarbonate, alkaline-earth metal bicarbonates, or bicarbonate salts of a transition metal ion, a protonated primary, secondary or tertiary amine, or a quaternary amine such as ammonium bicarbonate. Such bicarbonate salts may dissociate in solution to form bicarbonate anions and possibly carbonate anions. Carbon dioxide gas-releasing compositions can be used in greenhouses by applying it to the soil surface to enrich the air surrounding plants. The carbon dioxide-releasing compositions can also be used in modified atmosphere packaging by placing the composition within a package, exposing the composition to electromagnetic energy to generate carbon dioxide, and sealing the package to create a carbon dioxide atmosphere within the package. The package can then be used to control respiration of produce, cut flowers or other plants during storage and transportation, or to retard, prevent, inhibit or control biochemical decomposition of foods.

A nitrogen oxide such as nitrogen dioxide or nitric oxide is generated and released from a composition if it contains a source of nitrite anions. Suitable sources of nitrite anions include alkali metal nitrites such as sodium nitrite or potassium nitrite, alkaline-earth metal nitrites such as calcium nitrite, or nitrite salts of a transition metal ion, a protonated primary, secondary or tertiary amine, or a quaternary amine. Nitrogen dioxide or nitric oxide gas-releasing powders can be used to improve biocompatibility of biomaterials and for modified atmosphere packaging.

Ozone gas or hydrogen peroxide is generated and released if the composition contains a source of peroxide anions. Suitable ozone sources that can be incorporated into the composition include alkali metal peroxides such as sodium peroxide or potassium peroxide, alkaline-earth metal chlorites such as calcium peroxide, or peroxide salts of a transition metal ion, a protonated primary, secondary or tertiary amine, or a quaternary amine. Ozone-or hydrogen peroxide-releasing compositions can be used to deodorize, enhance freshness, retard, prevent, inhibit, or control chemotaxis, retard, prevent, inhibit or control biochemical decomposition, or to kill, retard, control or prevent the growth of bacteria, molds, fungi, algae, protozoa, and viruses.

In some instances, compositions contain two or more different anions to release two or more different gases at different rates. The gases are released for different purposes, or so that one gas will enhance the effect of the other gas. For example, a composition containing bisulfite and chlorite anions may release sulfur dioxide for food preservation and chlorine dioxide for deodorization, freshness enhancement, control of chemotaxis, or control of microorganisms.

Any electromagnetic energy source capable of activating an energy-activated catalyst of the invention can be used to generate a gas from the composition. In other words, any electromagnetic energy source that provides a photon having energy in excess of the band gap of the energy-activated catalyst is suitable. Preferred electromagnetic energy sources include light, such as sunlight, fluorescent light, and ultraviolet light, for photo-activation of the composition. Ultraviolet light and visible light other than incandescent light, such as blue light, are preferred sources of electromagnetic energy. Additives such as UV blockers can also be included in the composition if it is desirable to limit the wavelength range transmitted to the energy-activated catalyst. Photosensitizers can be added to shift the absorption wavelength of the composition, particularly to shift an ultraviolet absorption wavelength to a visible absorption wavelength to improve activation by room lighting. UV absorbers can be added to the composition to slow the gas generation and release rate.

Any semiconductor activated by electromagnetic energy, or a particle or other material incorporating such a semiconductor, can be used as the energy-activated catalyst of the composition. Such semiconductors are generally metallic, ceramic, inorganic, or polymeric materials prepared by various processes known in the art, such as sintering. The semiconductors can also be surface treated or encapsulated with materials such as silica or alumina to improve durability, dispersibility or other characteristics of the semiconductor. Catalysts for use in the invention are commercially available in a wide range of particle sizes from nanoparticles to granules. Representative energy-activated catalysts include metal oxides such as anatase, rutile or amorphous titanium dioxide ($TiO_2$), zinc oxide (ZnO), tungsten trioxide ($WO_3$), ruthenium dioxide ($RuO_2$), iridium dioxide ($IrO_2$), tin dioxide ($SnO_2$), strontium titanate ($SrTiO_3$), barium titanate ($BaTiO_3$), tantalum oxide ($Ta_2O_5$), calcium titanate ($CaTiO_3$), iron (III) oxide ($Fe_2O_3$), molybdenum trioxide ($MoO_3$), niobium pentoxide ($NbO_5$), indium trioxide ($In_2O_3$), cadmium oxide (CdO), hafnium oxide ($HfO_2$), zirconium oxide ($ZrO_2$), manganese dioxide ($MnO_2$), copper oxide ($Cu_2O$), vanadium pentoxide ($V_2O_5$), chromium trioxide ($CrO_3$), yttrium trioxide ($YO_3$), silver oxide ($Ag_2O$), or $Ti_xZr_{1-x}O_2$ wherein x is between 0 and 1; metal sulfides such as cadmium sulfide (CdS), zinc sulfide (ZnS), indium sulfide ($In_2S_3$), copper sulfide ($Cu_2S$), tungsten disulfide ($WS_2$), bismuth trisulfide ($BiS_3$), or zinc cadmium disulfide ($ZnCdS_2$); metal chalcogenites such as zinc selenide (ZnSe), cadmium selenide (CdSe), indium selenide ($In_2Se_3$), tungsten selenide ($WSe_3$), or cadmium telluride (CdTe); metal phosphides such as indium phosphide (InP); metal arsenides such as gallium arsenide (GaAs); nonmetallic semiconductors such as silicon (Si), silicon carbide (SiC), diamond, germanium (Ge), germanium dioxide ($GeO_2$) and germanium telluride (GeTe); photoactive homopolyanions such as $W_{10}O_{32}^{-4}$; photoactive heteropolyions such as $XM_{12}O_{40}^{-n}$ or $X_2M_{18}O_{62}^{-7}$ wherein x is Bi, Si, Ge, P or As, M is Mo or W, and n is an integer from 1 to 12; and polymeric semiconductors such as polyacetylene. Transition metal oxides such as titanium dioxide and zinc oxide are preferred because they are chemically stable, non-toxic, inexpensive, exhibit high photocatalytic activity, and are available as nanoparticles useful in preparing transparent formed or extruded plastic products.

In a second embodiment for controlled sustained release of a gas, a gas such as chlorine dioxide can be generated from an organic moisture activated composition. Organic moisture activated compositions are described in U.S. Pat. Nos. 5,360,609, 5,631,300, 5,639,295, 5,650,446, 5,668,185, 5,695,814, 5,705,092, 5,707,739, 5,888,528, 5,914,120, 5,922,776, 5,980,826, and 6,046,243.

Said organic moisture activated gas-releasing compositions generally comprise a hydrophilic material, a hydrophobic material and anions that form a gas when the composite is exposed to moisture. The composition may be, for example, a dispersion composed of hydrophilic and hydrophobic phases, or a mechanical combination of the hydrophilic and hydrophobic materials, such as powders and adjacent films. The powder has a hydrophobic core embedded with hydrophilic particles containing anions such as chlorite containing particles. Adjacent films comprise separate layers of the hydrophilic or hydrophobic materials.

Preferably, the gas-releasing composition comprises between about 5.0 wt. % and about 95 wt. % hydrophilic material and between about 5.0 wt. % and about 95 wt. % hydrophobic material, more preferably between about 15 wt.

% and about 95 wt. % hydrophilic material and between about 15 wt. % and about 95 wt. % hydrophobic material. If the composition is a dispersion, either material can form the continuous phase. The continuous phase constitutes between about 15 wt. % and about 95 wt. % of the dispersion and the dispersed phase constitutes between about 5 wt. % and about 85 wt. % of the dispersion, and preferably, the continuous phase constitutes between about 50 wt. % and about 95 wt. % of the dispersion and the dispersed phase constitutes between about 5 wt. % and about 50 wt. % of the dispersion.

The hydrophobic material of the gas-releasing component can be composed entirely of an acid releasing agent or can comprise the acid releasing agent in combination with a diluent, dispersant and/or a plasticizer. Any acid releasing agent that is capable of being hydrolyzed by ambient moisture is acceptable for purposes of the present invention.

The hydrophobic material comprises between about 10 wt. % and about 100 wt. % of the acid releasing agent, up to about 80 wt. % diluent, up to about 20 wt. % dispersant, and up to about 60 wt. % plasticizer, and preferably, between about 40 wt. % and about 100 wt. % of the acid releasing agent, between about 20 wt. % and about 80 wt. % diluent, between about 1 wt. % and about 10 wt. % dispersant, and up to about 20 wt. % plasticizer.

Suitable acid releasing agents include carboxylic acids, esters, anhydrides, acyl halides, phosphoric acid, phosphate esters, trialkylsilyl phosphate esters, dialkyl phosphates, sulfonic acid, sulfonic acid esters, sulfonic acid chlorides, phosphosilicates, phosphosilicic anhydrides, carboxylates of poly α-hydroxy alcohols such as sorbitan monostearate or sorbitol monostearate, phosphosiloxanes, and an acid releasing wax, such as propylene glycol monostearate acid releasing wax. Inorganic acid releasing agents, such as polyphosphates, are also preferred acid releasing agents because they form odorless powders generally having greater gas release efficiency as compared to powders containing an organic acid releasing agent. Suitable inorganic acid releasing agents include tetraalkyl ammonium polyphosphates, monobasic potassium phosphate, potassium polymetaphosphate, sodium metaphosphates, borophosphates, aluminophosphates, silicophosphates, sodium polyphosphates such as sodium tripolyphosphate, potassium tripolyphosphate, sodium-potassium phosphate, and salts containing hydrolyzable metal cations such as zinc. Preferably, the acid releasing agent does not react with the hydrophilic material, and does not exude or extract into the environment.

The hydrophobic material can include a diluent such as microcrystalline wax, paraffin wax, synthetic wax such as chlorinated wax or polyethylene wax, or a polymer such as atactic polypropylene, polyolefin, or polyester, or polymer blends, multicomponent polymers such as copolymers or terpolymers, or polymer alloys thereof.

The dispersant in the hydrophobic material is any substance that controls release of the gas from the composite, lowers the surface reactivity of the hydrophilic material, and does not react with the hydrophilic material. Substances having hydrophilic and hydrophobic portions are preferred. The hydrophilic portion of the substance can be absorbed by the surface of the hydrophilic material. Preferred dispersants that can be incorporated into the hydrophobic material have a melting point not greater than 150° C., and include amides of carboxylates such as amide isostearates, polyvinyl acetates, polyvinyl alcohols, polyvinylpyrrolidone copolymers, and metal carboxylates such as zinc isostearate.

Plasticizers can also be incorporated in either the hydrophobic or hydrophilic materials as is known in the art. Generally, formamide, isopropylacrylamide-acrylamide, N-methylacetamide, succinamide, N-ethylacetamide, N-methylformamide, N-ethylformamide, and amido substituted alkylene oxides are acceptable plasticizers.

Conventional film forming additives can be added to the hydrophobic and hydrophilic materials as needed. Such additives include crosslinking agents, flame retardants, emulsifiers and compatibilizers.

The hydrophilic material of the gas-releasing component can be composed entirely of a source of anions which react with hydronium ions to form the gas or can comprise the anion source in combination with another hydrophilic material. The hydrophilic material preferably contains an amine, an amide or an alcohol, or a compound containing amino, amido or hydroxyl moieties and having a high hydrogen bonding density. A source of anions is incorporated in the hydrophilic material and preferably constitutes between about 2 wt. % and about 40 wt. % of the hydrophilic material in the form of anions and counterions, and more preferably, between about 8 wt. % and about 10 wt. % of the hydrophilic material. The anions generally do not react with the hydrophilic material, but are surrounded by hydrogen bonds contributed by the nitrogen or hydroxide within the hydrophilic material.

Preferred amides for use as the hydrophilic material include formamide, acrylamide-isopropylacrylamide, copolymers of formamide and acrylamide-isopropylacrylamide, and copolymers of acrylamide, isopropylacrylamide or N,N-methylene bisacrylamide and a primary amine or a secondary amine. Such amides can be useful vehicles for film casting prior to exposure to chlorine dioxide, which does not react with polymerizable, electron deficient alkenes such as acrylamide.

Suitable amines for use as the hydrophilic material include primary amines, secondary amines, and tertiary amines having pendant hydrogen bonding groups. An amine substituted with electron donating groups which donate electrons to convert chlorine dioxide to chlorite is preferred. Electron withdrawing groups concentrate electron density at such groups such that it is difficult for the chlorine dioxide to extract an electron from the amine. Tertiary amines having non-hydrogen bonding pendant groups which are dissolved in a hydrophilic solvent are also acceptable.

Preferred amines include monoethanolamine, diethanolamine, triethanolamine, a copolymer of 1,3-diaminopropane or 1,2-diaminoethane and N,N-methylene bisacrylamide, 4-dimethylaminopyridine, tetramethylene ethylene diamine, N,N-dimethylamino cyclohexane, solubilized 1-(N-dipropylamino)-2-carboxyamido ethane or 1-(N-dimethylamino)-2-carboxyamido ethane, a primary amine having the formula $R_1NH_2$, a secondary amine having the formula $R_2R_3NH$, $N-(CH_2CH_2-OH)_3$,

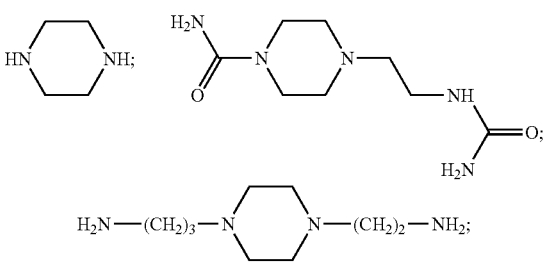

solubilized NR$_5$R$_6$R$_7$, (CH$_3$)$_2$NCH$_2$CH$_2$N(CH$_3$)$_2$, R$_8$R$_9$NCH$_2$CH$_2$C(O)NH$_2$, R$_{10}$N(NCH$_2$CH$_2$C(O)NH$_2$)$_2$, R$_{11}$R$_{12}$N(CH$_2$)$_3$NHC(O)NH$_2$, N(CH$_2$CH$_2$NHC(O)NH$_2$)$_3$,

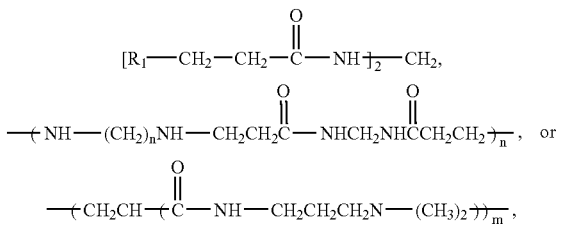

wherein: R$_1$ is —CH$_2$CH$_2$OCH$_2$CH$_2$OH, —C(CH$_3$)$_2$CH$_2$OH, —CH$_2$CH$_2$NHCH$_2$CH$_2$OH, —CH(CH$_3$)$_2$, —CH$_2$CH$_2$OH,

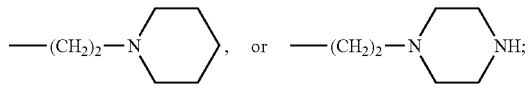

R$_2$ and R$_3$ are, independently, hexyl, benzyl, n-propyl, isopropyl, cyclohexyl, acrylamide, or —CH$_2$CH$_2$OH; R$_4$ is cyclohexyl or benzyl; R$_5$ and R$_6$ are methyl; R$_7$ is cyclohexyl or 4-pyridyl; R$_8$ and R$_9$ are, independently, methyl, n-propyl or isopropyl; R$_{10}$ is n-C$_6$H$_{13}$ or n-C$_2$H$_{25}$; R$_{11}$ and R$_{12}$ are, independently, methyl, ethyl, n-propyl or isopropyl; m is an integer from 1 to 100; and n is 2 or 3. Suitable diluents include formamide or acrylamide-isopropyl acrylamide. Oligomeric or polymeric secondary amines converted to acrylamide substituted tertiary amines by Michael reaction with acrylamides are also suitable because the amide group does not react with the acid releasing agent.

Hydroxylic compounds, including ethylene glycol, glycerin, methanol, ethanol, methoxyethanol, ethoxyethanol or other alcohols, can be used as the hydrophilic material. However, chlorine dioxide release can occur very rapidly when a hydroxylic compound is incorporated in the composite and can limit the applications for such composites to rapid chlorine dioxide releasing systems.

The hydrophobic and hydrophilic materials are substantially free of water to avoid significant release of chlorine dioxide prior to use of the composite. For purposes of the present invention, a hydrophilic material, a hydrophobic material, or a dispersion thereof is substantially free of water if the amount of water in the composite does not provide a pathway for transmission of hydronium ions from the hydrophobic material to the hydrophilic material. Generally, each of the hydrophilic and hydrophobic materials can include up to about 0.1 wt. % water without providing such a pathway for interdiffusion between the materials. Preferably, each material contains less than about $1.0 \times 10^{-3}$ wt. % water, and, more preferably, between about $1 \times 10^{-2}$ wt. % and about $1 \times 10^{-3}$ wt. % water. Insubstantial amounts of water can hydrolyze a portion of the acid releasing agent to produce acid and hydronium ions within the composite. The hydronium ions, however, do not diffuse into the hydrophilic material until enough free water is present for transport of hydronium ions.

When the anion source is a salt, the salt dissociates in the hydrophilic material such that the hydrophilic material in the composite will include anions and counterions. Suitable salts include those listed above for use in the energy-activated compositions.

The gas released by the composite will depend upon the anions within the hydrophilic material. Any gas that is formed by reaction of a hydronium ion and an anion can be generated and released by the composite. The gas is preferably selected from those listed above for the energy-activated compositions.

The moisture activated organic composites can be formulated in various ways to accommodate a wide range of end use applications. The composite can be formulated as an extrudate, such as a sheet (including films), or pellets, or as a powder using conventional extrusion and spray drying methods, respectively. The composite may be, for example, a dispersion composed of hydrophilic and hydrophobic phases, or a mechanical combination of the hydrophilic and hydrophobic materials, such as adjacent films. Adjacent films comprise separate layers of the hydrophilic or hydrophobic materials. The composites can also be formulated in solvents to allow for film casting or other application methods. The composite can be applied as a film by using well known hot melt, dip coat, spray coat, curtain coat, dry wax, wet wax, and lamination processes. Methods of making such composites are known in the art as in U.S. Pat. No. 5,705,092.

In a third embodiment for controlled sustained release of a gas, a gas such as chlorine dioxide can be generated from an inorganic moisture-activated composition. Inorganic moisture activated compositions (e.g., Microsphère® powder (Bernard Technologies)) are described in copending U.S. patent application Ser. No. 09/138,219 and U.S. Pat. Nos. 5,965,264 and 6,277,408.

A problem recognized in the art is disproportionation of chlorite in chlorite-containing particles to chlorate and chlorite when exposed to temperatures above about 160° C. This temperature limitation has obviated desired high temperature processing applications such as melt processing or sintering in which the chlorite is incorporated, for example, into extruded sheets (including films), body coverings or coatings.

For such high temperature applications the gas-releasing composition may be formulated as a powder as described in copending U.S. patent application Ser. No. 09/138,219 and U.S. Pat. No. 6,277,408, and sold under the Microsphère® trademark.

The powder comprises a particle having an acid releasing layer on an outer surface of the particle. The particle is comprised of anions dissolved within an amorphous, paracrystalline or crystalline solid solution. The anions are capable of reacting with hydronium ions to generate a gas. The particle contains one or more phases, which may be amorphous, paracrystalline or crystalline, with the anions dissolved in one or more of the phases. In these phases, the dissolved anions are either randomly distributed (e.g., a solid solution), or distributed in an ordered crystalline lattice in which the anions are substantially prevented from being neighbors. Hence, the anions can be an interstitial component of an alloy or other crystalline solid solution, or can be dissolved in a glass or other amorphous or paracrystalline solid solution. In any case, the solute anions are dispersed at the ionic level within the solvent. Such co-dissolution of anions and a material capable of forming an amorphous, paracrystalline or crystalline solid solution with the anions, elevates the disproportionation temperature above that of the anionic compound alone.

A paracrystalline solid solution is generally a material having one or more phases that exhibit some characteristics of a crystalline state as demonstrated, for example, by broadening of the reflections in the x-ray diffraction pattern. The amorphous, paracrystalline or crystalline material is not a zeolite or other material which must be heated at a temperature that would destroy the anions in order to dissolve the anions in the material. Preferably, the particle is comprised of a substantially amorphous silicate. For purposes of the present invention, the term "substantially amorphous" is defined as including no more than 20% crystalline inclusions, preferably no more than 10%, and more preferably no more than 2%.

The silicate particle is preferably in the form of a substantially amorphous silicate matrix in which the anions are uniformly dispersed and encapsulated. The silicate particles generally range in size between about 0.1 and about 1,000 microns depending upon the intended end use, and can be made of any size possible via any solid forming process, but preferably via spray drying. The silicate particles are either solid or hollow, and are generally substantially spherical. The particle may include an inert core which can be any porous or nonporous particle that is insoluble in water or an aqueous solution of a water miscible organic material, such as a clay, ceramic, metal, polymer or zeolite material.

In the case of a solid solution formed from chlorite anions and soluble silicate, it is believed that the chlorite anions are separated within the silicate matrix thus inhibiting chlorite anion intermolecular interaction resulting in elevated chlorite disproportion temperature on the order of about 220° C. Preferably, each silicate particle comprises between about 3 wt. % and about 95 wt. % silicate, between about 1 wt. % and about 30 wt. % anions capable of reacting to generate a gas, and up to about 95 wt. % inert core. More preferably, the silicate particle comprises between about 4 wt. % and about 95 wt. % silicate, between about 1 wt. % and about 15 wt. % anions capable of reacting to generate a gas, and up to about 95 wt. % of an inert core.

The silicate particle is substantially free of water to minimize diffusion of the anions into solution when further processing the particle, such as when the particles are added to an aqueous slurry containing an acid releasing agent to form a powder for sustained release of a gas. For purposes of the present invention, the silicate particle is substantially free of water if the amount of water in the silicate particle does not provide a pathway for transmission of anions from the particle into a solvent. Preferably, each of the silicate particles includes up to about 10 wt. %, preferably up to about 5 wt. % water without providing such a pathway for diffusion from the particle to the solvent.

Any silicate that is soluble in water or a water solution of a water miscible organic material, such as an alcohol, acetone or dimethylformamide, can be used in the silicate particles of the invention. Suitable silicates include sodium silicate, sodium metasilicate, sodium sesquisilicate, sodium orthosilicate, borosilicates, and aluminosilicates.

The anions contained in the silicate particles which react with hydronium ions to form a gas and the acid releasing agents are as described above for the energy-activated compositions.

The silicate particles optionally contain a base or a filler. The base controls release of gas from the particle by reacting with hydronium ions that diffuse into the particle from an acid releasing layer or interdiffuse into the anion-rich areas of the particle to form a salt. When the base is depleted, excess hydronium ions then react with the anions within the particle to form a gas. The filler controls release of a gas by creating a barrier to diffusion of hydronium ions. The silicate particle preferably includes a base or filler if chlorite anions are present in the particle to stabilize the chlorite during preparation of the particle or a powder containing the particle. Any base that reacts with a hydronium ion or any filler can be incorporated in the silicate particle.

Alternatively, the powder can be formulated as a single phase or as an interpenetrating network. A powder is comprised of a plurality of the particles containing an interpenetrating network. The interpenetrating network contains an amorphous, paracrystalline or crystalline solid solution, anions that are capable of reacting with hydronium ions to generate a gas, and an acid releasing agent. The solid solution of the interpenetrating network is preferably a substantially amorphous material. A substantially water-insoluble silicate preferably surrounds the interpenetrating network to minimize diffusion of the anions into the solution used to prepare the powder so as to minimize loss of anions needed to generate a gas. Alternatively, the solid solution of the interpenetrating network can contain a water-soluble silicate. For purposes of the present invention, an "interpenetrating network" is a material comprised of two or more phases in which at least one phase is topologically continuous from one free surface to another. The particles 60 are either solid or hollow, and are generally substantially spherical. The powders preferably are about 0.1 microns to about 1 millimeter in size.

In another embodiment, the powder is prepared from particles comprised of a single phase amorphous, paracrystalline or crystalline solid solution. Preferably, the solid solution contains a water-soluble silicate, anions that are capable of reacting with hydronium ions to generate a gas, and an acid releasing agent. The powder can also include particles containing an anhydrous material which contact an outer surface of the particle or are embedded in the particle. The anhydrous material is capable of binding with water. The powder is substantially free of water to avoid release of gas prior to use of the powder.

Another inorganic moisture-activated composition is a powder containing a molecular sieve core encased within an acid releasing agent as described above for the energy-activated compositions. The core contains anions such as those described above for the energy-activated compositions. The core of each particle is generally a molecular sieve particle containing anions. Any molecular sieve can be used in the powders of the invention including natural and synthetic molecular sieves. Suitable molecular sieves include natural and synthetic zeolites such as clinoptiloite, analcite, analcime, chabazite, heulandite, natrolite, phillipsite, stilbite, thomosonite and mordenite, crystalline aluminophosphates, ferricyanides and heteropolyacids. Molecular sieves generally have a pore size ranging from about 5 to 10 Angstroms, and a particle size ranging from about 10 micrometers to about one centimeter.

EXAMPLES

The following examples are provided for illustrative purposes only and are not intended to limit the scope of the present invention.

Example 1

Microlite® powder was incorporated into a vinyl glove to impart antimicrobial properties to the glove and to the immediate and proximal surfaces both in direct contact with the glove and in close proximity to the glove.

A number of studies were performed incorporating Microlite® powder and dispersants directly into a plastisol formulation. A glove form was then dipped into the stirred plastisol formulation. The resultant coating was allowed to dry under conventional conditions for vinyl glove formation. The gloves were prepared and packaged in a no light environment or a low light environment (i.e., less than about three ft candles of light) to avoid or minimize generation of gas prior to use of the gloves. The plastisol formulations included the following:

(a) Microlite® powder: about 0.5-20 wt. %, preferably about 5-8 wt. %;

(b) Disperplast® 1150 dispersing agent (available from BYK-Chemie of Wesel, Germany): about 0.01-3 wt. %, preferably about 0.1-0.3 wt. %

(c) Disperplast® BKY-410 thixotropic agent (available from BYK-Chemie of Wesel, Germany): about 0.005-3 wt. %, preferably about 0.02-0.1 wt. %

(d) Vinyl plastisol: remainder of formulation

The dispersing agent well distributes the Microlite® powder in the glove material. The thixotropic agent reduces sedimentation in the plastisol.

In a preferred embodiment, the plastisol formulation is prepared by adding the dispersing agent to the vinyl plastisol, then adding the Microlite® powder, and finally the thixotropic agent, with stirring, followed by deaeration and processing as for standard vinyl gloves, however under darkened conditions. Gloves are produced and packaged under dark or low light conditions (i.e., less than about three ft candles), and are packaged in dispenser boxes, or other suitable packaging.

Light activation of the formed vinyl gloves was evaluated over a three hour time using normal room fluorescent lighting. Light activation % in table 1 a represents the percentage of the maximum chlorine dioxide release. An electrochemical cell was used to measure the activation %. The data is reported in Table 1 a for an average of ten gloves.

TABLE 1a

| Light Exposure Time (min) | Light Activation (%) |
|---|---|
| 0 | 0 |
| 6 | 33 |
| 12 | 57 |
| 18 | 70 |
| 24 | 88 |
| 30 | 92 |
| 36 | 100 |
| 42 | 95 |
| 48 | 93 |
| 54 | 90 |
| 60 | 82 |
| 90 | 66 |
| 120 | 50 |
| 150 | 41 |
| 180 | 32 |

Efficacy of the formed vinyl gloves inoculated with *Staphylococcus aureus* was evaluated over a two hour time period using normal room fluorescent lighting for activation. The data is reported in Table 1b for an average of three gloves.

TABLE 1b

| % *Staph.* Reduction | Light Exposure Time (min) |
|---|---|
| 0 | 0 |
| 99.95 | 15 |
| 99.98 | 30 |
| 99.99 | 60 |
| 99.992 | 120 |

The formed vinyl gloves were evaluated against the physical and dimensional properties of ASTM D5250-00 for medical vinyl gloves and were tested according to method ASTM 5250 with results reported in Table 1c below.

TABLE 1c

| Test Parameter | Unit | Acceptance criterion | Result |
|---|---|---|---|
| Total Glove Length (ave) | mm | >230 | 249 |
| Total Glove Length (% std dev) | % | | 0.7% |
| Total Glove Length (min) | mm | | 245 |
| Palm Thickness (ave) | mm | >0.08 | 0.13 |
| Palm Thickness (% std dev) | % | | 2.9% |
| Palm Thickness (min) | mm | | 0.12 |
| Finger Thickness (ave) | mm | >0.05 | 0.22 |
| Finger Thickness (% std dev) | % | | 7.4% |
| Finger Thickness (min) | mm | | 0.20 |
| Tensile Strength (ave) | MPa | >9 | 13.0 |
| Tensile Strength (% std dev) | % | | 2.3% |
| Tensile Strength (min) | MPa | | 12.5 |
| Elongation (ave) | % | >300 | 408 |
| Elongation (% std dev) | % | | 1.0% |
| Elongation (min) | % | | 400 |
| Pin Hole | AQL* | 4.0 | 4.0 |

*Acceptance Quality Level

Gloves produced in this manner demonstrate activation by light with generation of chlorine dioxide and reduction in bacteria when exposed to various organisms in a microbiological test. These gloves also have mechanical properties such as tensile strength and elongation that are comparable to that of commercially available vinyl gloves without antimicrobial properties.

Example 2

Microlite® particles were incorporated into a pigmented vinyl glove to impart antimicrobial properties to the glove and to the immediate and proximal surfaces both in direct contact with the glove and in close proximity to the glove.

Blue pigment, Microlite® powder and dispersants directly incorporated into a plastisol formulation. A glove form was then dipped into the stirred plastisol formulation. The resultant coating was allowed to dry under conventional conditions for vinyl glove formation. The gloves were prepared and packaged in a no light environment or a low light environment (i.e., less than about three ft candles of light) to avoid or minimize generation of gas prior to use of the gloves.

The plastisol formulation included the following:

(a) Microlite® powder: about 10 wt. %;

(b) Disperplast® 1150 dispersing agent (available from BYK-Chemie of Wesel, Germany): about 0.3 wt. %;

(c) Disperplast® BKY-410 thixotropic agent (available from BYK-Chemie of Wesel, Germany): about 0.1 wt. %;

(d) Blue color pigment; and (d) Vinyl plastisol: remainder of formulation.

The plastisol formulation is preferably prepared by adding the dispersing agent to the vinyl plastisol, then adding the Microlite® powder, blue pigment and finally the thixotropic agent, with stirring, followed by deaeration and processing as for standard vinyl gloves, however under darkened conditions.

Chlorine dioxide generation in ppm was evaluated in a sealed chamber over a period of about 2.5 hours at using normal room fluorescent lighting for activation and an electrochemical cell for determining chlorine dioxide concentration. The data is reported in Table 2 below.

TABLE 2

| ClO2 (ppm) | Light Exposure Time (min) |
|---|---|
| 0 | 0 |
| 0 | 6 |
| 1.20 | 17 |
| 2.50 | 20 |
| 3.10 | 24 |
| 3.30 | 30 |
| 2.80 | 33 |
| 2.30 | 37 |
| 1.80 | 43 |
| 1.50 | 48 |
| 1.20 | 53 |
| 1.00 | 58 |
| 0.80 | 63 |
| 0.65 | 67 |
| 0.55 | 73 |
| 0.50 | 77 |
| 0.40 | 83 |
| 0.35 | 88 |
| 0.30 | 92 |
| 0.25 | 98 |
| 0.20 | 103 |
| 0.20 | 108 |
| 0.15 | 113 |
| 0.15 | 118 |
| 0.10 | 122 |
| 0.10 | 127 |

Example 3

Microbiological Testing of the Antimicrobial Effectiveness of Chlorine Dioxide Emitting Polyethylene Gloves with Inoculations on the Glove and Hand Test Protocol:

Organisms. Three pathogenic (disease-causing) organisms were used for testing on the outer surfaces of the gloves: *Escherichia coli* O157:H7, *Salmonella Typhimurium*, and *Listeria monocytogenes*. Two nonpathogenic bacterial contaminants of hands were used in this investigation for direct inoculation on the hands: generic *Escherichia coli* and *Staphylococcus aureus*.

Subjects. Three volunteer adult human subjects, having signed informed consent forms, participated in this study.

Application of bacterial cells to the hands and bacterial sampling. For inoculation of the hands, two cotton swabs were dipped into the bacteria suspension (generic *E. coli* and *S. aureus*) and rubbed on the surface of the palm and back of previously washed and sanitized hands. On one hand, a glove containing chlorine dioxide generating material was applied and the other hand wore a control commercially available polyethylene glove. The volunteers placed their hands in fluorescent lighting (Cool White) with the source emitting from the top and bottom simultaneously. The exposure times to the fluorescent light were 0, 5, 20, and 45 minutes.

For the inoculated hands, the gloves were carefully removed and the hands massaged for 2 minutes in a neutralizing broth to counteract the antimicrobial effects of the chlorine dioxide. This broth was used to enumerate viable inoculated bacteria from the hands.

Application of bacterial cells on the glove. A non-sterile latex exam glove was placed on each hand to minimize the transfer of bacteria from the hand to the polyethylene glove. A control polyethylene glove (left hand) and a chlorine dioxide emitting polyethylene glove (right hand) were donned. The palm and back of the hand portion of the glove exterior were inoculated separately with *E. coli* O157:H7, *S. typhimurium*, and *L. monocytogenes* cells. The palm and back of the hand area were inoculated using two sterile cotton swabs dipped in the cell suspension. The inoculum on the gloves was allowed to air dry for 2 minutes. The volunteers placed their hands in fluorescent lighting (Cool White) with the source emitting from the top and bottom simultaneously. The exposure times to the fluorescent light were 0, 5, 20, and 45 minutes.

Gloves were removed from the hands, placed in stomacher bags containing neutralizing broth and pummeled for 2 minutes at high speed. The remaining viable bacteria were enumerated.

Enumeration of bacteria. The pour plate technique was used to enumerate the bacteria. Duplicate plates at each dilution were used. Plates were incubated at 35° C. for 24 to 48 hours. After incubation, the Colony Forming Unites (CFUs)/area were converted to $\log_{10}$ and the means determined. The diluent was sterile 0.1% peptone water.

Effect on Inoculated Hands. The chlorine dioxide generating gloves reduced the bacteria inoculated on the hands within five minutes of wearing the gloves. The amount of kill increased the longer the gloves were worn. More than a two-log reduction (over 99% kill) in 45 minutes occurred for *E. coli* (Table 3a) and *S. aureus* (Table 3b).

TABLE 3a

GENERIC *ESCHERICHIA COLI* ATTC 25922 INOCULATION ON THE HANDS Average Bacterial Reduction

| Sampling Time (min) | Average Reduction (Log10) | Average Reduction (%) |
|---|---|---|
| 0 | NA | NA |
| 5 | 0.93 | 87.54 |
| 20 | 1.45 | 96.57 |
| 45 | 2.12 | 99.25 |

NA = Nonapplicable

TABLE 3b

*STAPHYLOCOCCUS AUREUS* ATTC 6538 INOCULATION ON THE HANDS Average Bacterial Reduction

| Sampling Time (min) | Average Reduction (Log10) | Average Reduction (%) |
|---|---|---|
| 0 | NA | NA |
| 5 | 0.31 | 50.08 |
| 20 | 1.11 | 92.24 |
| 45 | 2.40 | 99.60 |

NA = Nonapplicable

Effect on Inoculated Gloves. The pathogenic bacteria inoculated on the outer portion of the chlorine dioxide emitting polyethylene glove, where cross-contamination may occur under normal use, were reduced by more than 90% in five minutes for *E. coli* O157:H7 (Table 3c) and *Listeria* (Table 3d), whereas, 70% of the inoculated *Salmonella* was killed (Table 3e). After 45 minutes of exposure to light, the active gloves reduced the *E. coli* by 99.999% (>4 logs killed), the *Salmonella* by 99.87%, and the *Listeria* by 97.87%.

TABLE 3c

ESCHERICHIA COLI O157:H7 ATTC 43894 INOCULATION ON THE GLOVES Average Bacterial Reduction

| Sampling Time (min) | Average Reduction (Log10) | Average Reduction (%) |
|---|---|---|
| 0 | NA | NA |
| 5 | 1.54 | 97.070 |
| 20 | 3.98 | 99.996 |
| 45 | 4.71 | 99.999 |

NA = Nonapplicable

TABLE 3d

LISTERIA MONOCYTOGENES ATTC 19114 INOCULATION ON THE GLOVES Average Bacterial Reduction

| Sampling Time (min) | Average Reduction (Log10) | Average Reduction (%) |
|---|---|---|
| 0 | NA | NA |
| 5 | 1.07 | 91.54 |
| 20 | 1.27 | 94.63 |
| 45 | 1.68 | 97.87 |

NA = Nonapplicable

TABLE 3e

SALMONELLA TYPHIMURIUM ATTC 6994 INOCULATION ON THE GLOVES Average Bacterial Reduction

| Sampling Time (min) | Average Reduction (Log10) | Average Reduction (%) |
|---|---|---|
| 0 | NA | NA |
| 5 | 0.54 | 70.06 |
| 20 | 1.14 | 92.86 |
| 45 | 2.91 | 99.87 |

NA = Nonapplicable

Example 4

Microbiological Testing of the Antimicrobial Effectiveness of Chlorine Dioxide Emitting Bags on *Bacillum Anthracis* Spores Test Protocol:

A culture of *Bacillus anthracis* spores (anthrax) was prepared and between one and two billion spores were applied to a paper test substrate.

After air-drying the inoculated substrates were sealed in a Kevlon® bag which was then placed in a zip lock bag and exposed at room temperature to standard cool white fluorescent lighting at an intensity level of about 300 foot candles for sampling time points of 2, 4 and 6 hours. Kevlon® bags are formed from polyethylene and contain 20% Microlite® powder, which contains the active ingredient sodium chlorite. The bags were turned every hour assuring uniformity of light to the Kevlon® material. Negative controls consisted of inoculated substrates placed in non-Kevlon® bags thereafter sampled at 0 and 6 hours.

At 2,4 and 6 hours the sealed bags were opened aseptically and the substrates placed into sterile TSB broth then mixed vigorously. The broth was serially diluted, cultured and used to enumerate the surviving *Bacillus anthracis* spores. The culture plates were incubated at 35° C. for 48 hours. The CFUs remaining were calculated and the data were converted to $\log_{10}$ and geometric means calculated. Results are reported in table 4.

TABLE 4

Kill of *Bacillus anthracis* Spores in Kevlon ® Bags

| Time (hours) | CFU Remaining | $\log_{10}$ Kill | % Kill |
|---|---|---|---|
| 0 | $1.45 \times 10^7$ | NA | 0 |
| 2 | $4.5 \times 10^3$ | 3.51 | >99.95 |
| 4 | <1 | >7.16 | >99.999992 |
| 6 | <1 | >7.16 | >99.999992 |

NA = not applicable

Kevlon® decontamination bags are capable of killing *Bacillus anthracis* (anthrax) spores within 4 hours of activation using standard fluorescent light. This study provides evidence for at least a 7 log kill.

Example 5

Skin Irritation Evaluation of Chlorine Dioxide Releasing Polymers

Test Protocol:

The level of primary skin irritation of chlorine dioxide releasing polyethylene, chlorine dioxide releasing vinyl, and non-chlorine dioxide releasing polyethylene and vinyl articles was evaluated on abraded and intact skin of six rabbits under occluded conditions. Chlorine dioxide releasing vinyl and polyethylene gloves were prepared as per the procedure of Examples 1, 2, 7 and 8. Commercially available standard vinyl and polyethylene gloves were used as controls.

A 2.5 by 2.5 cm piece of each test article was applied to each of two test areas, abraded and non-abraded, on each rabbit. Each area of application was covered with a 5 by 5 cm gauze patch secured with paper tape, overwrapped with a polyvinylidene chloride (PVDC) film (Saran Wrap®) and secured with non-tissue reactive adhesive tape (Elastoplast®, manufactured by Beiersdorf, Inc.) to maintain the test article contact with the skin under occluded conditions. Dermal irritation was evaluated at approximately 24, 48 and 72 hours post application.

Results:

Exposure of the chlorine dioxide releasing test articles and the commercial standards to the intact skin of six rabbits under 24-hour occluded conditions resulted in no dermal irritation or evidence of corrosion at the intact sites and no indication of corrosivity at any of the abraded sites. Moreover, the rabbits did not exhibit gross evidence of treatment-related toxicity during the course of the study. The chlorine dioxide releasing polyethylene, chlorine dioxide releasing vinyl, and the commercial standard non-chlorine dioxide releasing polyethylene and vinyl articles rate as non-irritating to intact skin based on the responses observed following dermal application on rabbits.

Example 6

Bacteria Count Reduction on Dental Implants

Dental implants, sieves, and forceps were sterilized in an autoclave at 121° C. for 20 minutes. After autoclaving this equipment was placed under a biological control atmosphere hood. A culture of *Bacillus subtilis* var. *niger* (concentration of 18 million spores/ml) was aseptically transferred to a sterile 30 ml beaker that was placed under the biological control atmosphere hood. The sterilized dental implants were aseptically removed by using a sterile forceps and dipped for 10 seconds in a culture of *Bacillus subtilis* var. *niger* (concentration of 18 million spores/ml). The inoculated implants were allowed to air dry for 20 minutes on a sterile sieve in the biological control atmosphere hood.

After air-drying, the dental implants were heat sealed in a Microlite® bag (2"×2.75") with a humidity packet containing 0.1 ml water. Microlite® bags are composed of monolayer or bilayer polyethylene film containing about 20% by weight of Microlite® powder. The humidity packet was made from Tyvek® material so direct water exposure to the implant did not occur. The Microlite® bag with implant and humidity packet was sealed in a small zip lock bag (3.5"×5") and exposed to fluorescent lighting at an intensity level of 8000 lux for 1, 2, and 3 hours. The fluorescent lighting was supplied by using a fixture containing 4 Sylvania Cool White Deluxe F40/CWX bulbs. The fixture was suspended 12 inches above the table holding the bagged implant samples. The bags were turned over every 30 minutes assuring uniformity of light to the Microlite® material. The temperature during exposure was nominally 25° C.

At 0, 1, 2, and 3 hours, the sealed bags were aseptically opened and the dental implants were removed using sterile forceps. The implants were placed into 10 ml of sterile DE Neutralizing broth and the contents of the tube vortexed for 1 minute. The DE Neutralizing broth was serially diluted. The pour plate technique using triplicate Tryptic soy agar (TSA) plating was utilized to enumerate the *B. subtilis* spores. The plates were incubated at 35° C. for 48 hours. The colony forming unit data were collected and converted to $\log_{10}$. The data are reported in table 6.

TABLE 6

| Description | Exposure Time (hrs) | Average Log10 CFU/implant | Log Reduction |
| --- | --- | --- | --- |
| Positive Control (A) | 0 | 6.73 | NA |
| Positive Control (B) | 0 | 6.96 | NA |
| Positive Control (C) | 0 | 7.08 | NA |
| Negative Control | 0 | <1 | NA |
| Positive Control | 1 | 6.99 | NA |
| Implant (A) | 1 | 5.74 | 1.25 |
| Implant (B) | 1 | 5.60 | 1.39 |
| Implant (C) | 1 | 5.56 | 1.43 |
| Positive Control | 2 | 6.65 | NA |
| Implant (A) | 2 | 0.60 | 6.05 |
| Implant (B) | 2 | 2.16 | 4.49 |
| Implant (C) | 2 | 0.85 | 5.80 |
| Positive Control | 3 | 6.87 | NA |
| Implant (A) | 3 | <0 | >6.87 |
| Implant (B) | 3 | <0 | >6.87 |
| Implant (C) | 3 | <0 | >6.87 |
| Negative Control | 3 | <0 | NA |

NA = Not Applicable

Example 7

This example evaluates the direct and indirect film contact of 0.45 micron filters through which approximately 100-200 test organisms had been filtered.

The test films were comprised of polyethylene and other components as follows: Green triclosan-containing film (a direct contact biocidal film), Wasaouro Film (allyl-isothiocyanate gas generating film), thin Microgàrde® Film (about 2 mil (0.005 cm) thick chlorine dioxide generating film available from Bernard Technologies, Inc. comprising about 20% loading of Microsphère® 2500 powder), thick Microgàrde® Film (about 4 mil (0.01 cm) thick chlorine dioxide generating film available from Bernàrd Technologies, Inc. comprising about 40% loading of Microsphère® 2500 powder). A non-biocidal polyethylene control film was also employed. All materials were stored at room temperature until used. Triclosan is a heterocyclic organic antimicrobial compound. Microsphère® 2500 powder contains the active ingredient sodium chlorite and is available from Bernard Technologies, Inc. Microgàrde® films were prepared by blending Microsphère® 2500 powder and polyethylene at the indicated concentrations and then forming the films to the desired thickness. Microorganisms used were *Escherichia coli, Staphylococcus aureus* and *Aspergillus niger.*

Test films were aseptically cut, if necessary, into 2×2 inch squares. For all samples, Whatman #2 filter paper was affixed, with tape, to the inner surface of the culture plate lid. For indirect contact (Setup B), test or control film was stapled to the Whatman #2 filter paper prior to taping to the Culture plate lid. The Whatman #2 filter paper was wetted with 1.5 ml sterile deionized water to raise the relative humidity within in the plate just prior introducing the filter containing the challenge organism or the direct inoculum. Test or Control film was taped to the sterile bottom of the culture plate using double-sided Scotch tape for the film samples. Tape was also added to wrap the culture plate to reduce moisture loss during exposure time.

The microorganisms used to challenge the films in this experiment were grown according to the conditions listed in Table 7a below. Bacterial cultures were centrifuged at 1,450×g for 30 minutes and the pellet resuspended in sterile 0.85% saline to obtain the OD reading listed in Table 7a (Milton Roy Spec 20 Spectrophotometer at 420 nm). The resuspended cells were further diluted to obtain a final concentration of approximately 200 CFU/50 ml with a total volume of 2600 ml. The cell suspensions were filtered in 50 ml aliquots through 0.45 μm disposable Nalgene filter units. For direct contact (Setup A), the filters were removed and placed directly onto one of the test or control films in the bottom portion of the Culture plate that had been prepared with filter paper as previously stated. For indirect contact (Setup B), the filter was placed directly into the bottom portion of the sterile Culture plate (film stapled to Whatman #2 filter paper in lid). Filtered organisms were exposed, in duplicate, to test or control films at either room temperature (25° C.) for 24 hours or 4° C. for 24 hours.

Mold spores had been previously collected and were stored in frozen culture. The spores were thawed at room temperature and serially diluted in 0.85% sterile saline to obtain the required volume for filtration. Mold spores were filtered and exposed as previously stated for the bacteria.

TABLE 7a

| Microbe | Media | OD @ 420 nm | Incubation Time/Temp |
| --- | --- | --- | --- |
| *E. Coli* | Difco brain hear infusion broth | 0.400 | 24 hours; 35° C. |
| *S. Aureus* | Difco brain hear infusion broth | 0.210 | 24 hours; 35° C. |

TABLE 7a-continued

| Microbe | Media | OD @ 420 nm | Incubation Time/Temp |
|---|---|---|---|
| A. Niger | Frozen spore suspension (in 0.85% saline) used directly after thawing | NA | NA |

NA = Not Applicable

After direct or indirect exposure to the test or control film at 4 or 25° C. for 24 hours (Setups A or B), the filters were analyzed for growth of target bacteria or mold, by aseptically transferring the filter to agar plates containing Difco Trypticase Soy Agar (for bacteria) or Difco Potato Dextrose Agar (for mold). Trypticase Soy agar plates were incubated for 48 hours at 35° C. and Potato Dextrose Agar plates were incubated for 72 hours at 25° C. The cultures were enumerated after incubation.

TABLE 7b

Efficacy in % control of films having indirect contact with microorganisms

| Microbe | Triclosan | Wasaouro ™ | Thin Film | Thick Film |
|---|---|---|---|---|
| A. niger (4° C.) | 0% | >99% | >99% | >99% |
| S. aureus (25° C.) | 10% | 5% | >99% | >99% |
| E. coli (4° C.) | 0% | 0% | >99% | >99% |

TABLE 7c

Efficacy in % control of films in close contact with microorganisms

| Microbe | Triclosan | Wasaouro ™ | Thin Film | Thick Film |
|---|---|---|---|---|
| A. niger (4° C.) | 15% | >99% | >99% | >99% |
| S. aureus (25° C.) | 0% | 0% | >99% | >99% |
| E. coli (4° C.) | 20% | 0% | >99% | >99% |

The result indicate that the thin and thick Microgàrde® Films generate a biocidal atmosphere that is effective against mold (*A. niger*), Gram negative bacteria (*E. coli*) and Gram positive bacteria (*S. aureus*). Wasaouro™ has activity against mold but is not active against bacteria. Triclosan containing film has no activity against the microorganisms in this study when the microorganisms are not in direct contact with the Triclosan.

Example 8

Determining Antimicrobial Activity of Chlorine Dioxide Generating Polymeric Film This example was done to determine antimicrobial effect of chlorine dioxide generated from polymeric film in the form of extruded film.

The polymeric films to be tested contain Microsphère® 2500 powder, a chlorine dioxide generating system that is activated by high relative humidity. The films were prepared by blending Microsphère® 2500 powder and low density polyethylene (LPDE) at the indicated concentrations and then forming the films to the desired thickness. The non-activated precursor film is not antimicrobial. The material in response to an activator generates a localized microatmosphere of chlorine dioxide gas. The chlorine dioxide gas is soluble in water, having a partition coefficient of 40 at 21° C., and is heavier than air. The polymeric film contains the precursors necessary to generate chlorine dioxide.

The test method used 0.2 micron filters impinged with a fixed number of microorganisms equally distributed over the surface of the filter as a means to expose the microorganism to the antimicrobial gas generated by the polymeric film specimens. These filters, following exposure to the polymeric film specimens, were then aseptically transferred to the surface of the appropriate nutrient agar culture dishes. The surviving microorganisms on the filter then grew to form a visible colony directly on the microporous filter. Such technique eliminates rinsing and extraction of microorganisms from other surfaces, the drying out of the test microorganisms and represents or simulates the environment most likely to be encountered by the polymeric films under commercial use.

The following bacteria were tested: *Escherichia coli* (generic) ATCC#25922; *Escherichia coli* O157:H7 ATCC#35150; *Listeria monocytogenes* ATTC#43249; *Pseudomonas fluorescens* ATTC#13525; and *Enterococcus faecium* ATTC#19434. The following yeast and fungi were tested: *Aspergillus niger* ATTC#16888 and *Zygosacchromyces bailii* ATTC#8766.

Each test specimen was placed in the bottom of a sterile culture dish. Sterile filter paper, approximately 50 to 75 mm diameter, was affixed with tape to the inner surface of the lid of each culture dish. The filter paper on the lid was wetted with 1.5 ml of sterile distilled water (to raise the relative humidity in the culture dish to at least 85%) just prior to introducing the microporous filter containing the challenge organisms.

The microporous filters were prepared with the microorganisms by filtering a dilute suspension of each microorganism through the filter using a vacuum assist. 300 ml of a microbial suspension of 200 Colony Forming Units (CFU) per 50 ml was passed through the 0.2 micron filter.

The filter was removed from the holder and transferred to the surface of the test specimen in the culture dish having a wetted filter paper on the lid. The culture dish was covered and transferred to a small container, such as a round polypropylene food storage container and then placed in the proper incubator.

Culture dishes with films and microbial filters are incubated for 24 hours. One set each at 25° C. and 4° C. After 24 hours incubation, each filter was removed aseptically and transferred to the nutrient agar (All Purpose Tween for bacteria and Potato Dextrose for yeast and mold) culture dishes and incubated to enable microbial growth of any surviving microorganisms. The agar dishes for the bacteria were incubated at 35° C. for 24 hours and the colony growth on each filter enumerated. The agar dishes for the yeast and mold were incubated at 25° C. for 72 hours and the colony growth on each filter enumerated.

For visible effects, the culture dishes were from the incubator(s) and rated as follows: No observed growth=0; Traces of growth (<10%)=1; Light growth (10-30%)=2; Medium growth (30-60%)=3; Heavy growth (60% to complete)=4. Traces of growth may be defined as scattered, sparse fungus growth such as might develop from a mass of spores in the original inoculum, or extraneous contamination. Continuous cobwebby growth extending over the specimen, even though not obscuring the specimen, should be rated a 2.

TABLE 8a

OD readings

| Microbe ATTC# | Media | OD Reading @ 420 nm | Incubation Time | Incubation Temp |
|---|---|---|---|---|
| 25922 | 1 | 0.400 | 24 hours | 35° C. |
| 35150 | 1 | 0.420 | 24 hours | 35° C. |
| 19434 | 1 | 0.490 | 24 hours | 35° C. |
| 43249 | 1 | 0.420 | 24 hours | 35° C. |
| 13525 | 2 | 0.440 | 24 hours | 25° C. |
| 8766 | 3 | NA | 72 hours | 25° C. |

1 = Difco Brain Heart Infusion Broth
2 = Difco All Purpose Tween Broth
3 = Difco Potato Dextrose Broth TABLE 8b Film sample compositions evaluated

| Film Type | % Microsphère ® 2500 powder | Resin | Thickness | Extrusion |
|---|---|---|---|---|
| Control | 0 | LDPE-2 mi | 4 mil (0.01 cm) | Blown |
| Test Film 1 | 8 | LDPE-2 mi | 4 mil (0.01 cm) | Blown |
| Test Film 2 | 5 | LDPE-2 mi | 10 mil (0.025 cm) | Cast |
| Test Film 3 | 10 | LDPE-2 mi | 10 mil (0.025 cm) | Cast |
| Test Film 4 | 20 | LDPE-2 mi | 10 mil (0.025 cm) | Cast |
| Test Film 5 | 50 | Dow 4012 | 15 mil (0.038 cm) | Cast |

TABLE 8c

Results

| Microbe | Film | Exposure Time/Temp | CFU microbe remaining |
|---|---|---|---|
| E. coli (generic) | Control | 24 hrs; R.T. | 2,000 |
| E. coli (generic) | Test Film 1 | 24 hrs; R.T. | <1 |
| E. coli (generic) | Test Film 2 | 24 hrs; R.T. | <1 |
| E. coli (generic) | Test Film 3 | 24 hrs; R.T. | <1 |
| E. coli (generic) | Test Film 4 | 24 hrs; R.T. | <1 |
| E. coli (generic) | Test Film 5 | 24 hrs; R.T. | <1 |
| E. coli (generic) | Control | 24 hrs; 4° C. | 10,000 |
| E. coli (generic) | Test Film 1 | 24 hrs; 4° C. | <1 |
| E. coli (generic) | Test Film 2 | 24 hrs; 4° C. | 28 |
| E. coli (generic) | Test Film 3 | 24 hrs; 4° C. | <1 |
| E. coli (generic) | Test Film 4 | 24 hrs; 4° C. | <1 |
| E. coli (generic) | Test Film 5 | 24 hrs; 4° C. | <1 |
| E. coli (O157:H7) | Control | 24 hrs; R.T. | 70 |
| E. coli (O157:H7) | Test Film 1 | 24 hrs; R.T. | <1 |
| E. faecuim | Control | 24 hrs; R.T. | 158 |
| E. faecuim | Test Film 1 | 24 hrs; R.T. | <1 |
| E. faecuim | Test Film 2 | 24 hrs; R.T. | <1 |
| E. faecuim | Test Film 3 | 24 hrs; R.T. | <1 |
| E. faecuim | Test Film 4 | 24 hrs; R.T. | <1 |
| E. faecuim | Test Film 5 | 24 hrs; R.T. | <1 |
| E. faecuim | Control | 24 hrs; 4° C. | 150 |
| E. faecuim | Test Film 1 | 24 hrs; 4° C. | 2 |
| E. faecuim | Test Film 2 | 24 hrs; 4° C. | 64 |
| E. faecuim | Test Film 3 | 24 hrs; 4° C. | <1 |
| E. faecuim | Test Film 4 | 24 hrs; 4° C. | <1 |
| E. faecuim | Test Film 5 | 24 hrs; 4° C. | <1 |
| Listeria mono. | Control | 24 hrs; R.T. | 134 |
| Listeria mono. | Test Film 1 | 24 hrs; R.T. | <1 |
| Listeria mono. | Control | 24 hrs; 4° C. | 159 |
| Listeria mono. | Test Film 1 | 24 hrs; 4° C. | 2 |
| Pseudo. Fluorescens | Control | 24 hrs; R.T. | 180 |
| Pseudo. Fluorescens | Test Film 1 | 24 hrs; R.T. | <1 |
| Pseudo. Fluorescens | Control | 24 hrs; 4° C. | 194 |
| Pseudo. Fluorescens | Test Film 1 | 24 hrs; 4° C. | <1 |
| Z. bailii | Control | 24 hrs; R.T. | 326 |
| Z. bailii | Test Film 1 | 24 hrs; R.T. | 11 |

TABLE 8c-continued

Results

| Microbe | Film | Exposure Time/Temp | CFU microbe remaining |
|---|---|---|---|
| Z. bailii | Control | 24 hrs; R.T. | 2,000 |
| Z. bailii | Test Film 1 | 24 hrs; R.T. | 9 |
| Z. bailii | Test Film 2 | 24 hrs; R.T. | 750 |
| Z. bailii | Test Film 3 | 24 hrs; R.T. | 3 |
| Z. bailii | Test Film 4 | 24 hrs; R.T. | <1 |
| Z. bailii | Test Film 5 | 24 hrs; R.T. | <1 |
| Z. bailii | Control | 24 hrs; 4° C. | 500 |
| Z. bailii | Test Film 1 | 24 hrs; 4° C. | 329 |
| Z. bailii | Control | 24 hrs; 4° C. | 2,000 |
| Z. bailii | Test Film 1 | 24 hrs; 4° C. | <1 |
| Z. bailii | Test Film 2 | 24 hrs; 4° C. | 1,000 |
| Z. bailii | Test Film 3 | 24 hrs; 4° C. | 450 |
| Z. bailii | Test Film 4 | 24 hrs; 4° C. | 8 |
| Z. bailii | Test Film 5 | 24 hrs; 4° C. | <1 |

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed:

1. A glove for reducing microbiological contamination and/or odor, the glove comprising a gas releasing monolayer, the gas releasing monolayer prepared from a composition comprising:
   from about 74% to about 99% by weight of a plastisol comprising PVC resin and a plasticizer;
   from about 0.005% to about 3% by weight of a thixotropic agent;
   from about 0.01% to about 3% by weight of a dispersing agent; and
   from about 0.5% to about 20% by weight of a gas-generating composition which is capable of generating and releasing at least one gas selected from chlorine dioxide, chlorine, sulfur dioxide, carbon dioxide and/or nitrous oxide,
   the gas being released from the glove upon exposure of a surface of the glove to light and/or humidity.

2. The glove of claim 1 wherein the surface is the interior surface of the glove.

3. The glove of claim 1 wherein the gas-generating composition comprises anions capable of being oxidized or reacted to generate the gas upon exposure to light and/or humidity.

4. The glove of claim 3 wherein the gas-generating composition comprises anions capable of reacting with hydronium ions to generate the gas upon exposure to humidity.

5. The glove of claim 1 wherein the glove contains a colorant capable of changing color when oxidized by the gas.

6. The glove of claim 1 wherein the composition is capable of generating and releasing at least one gas upon exposure to light.

7. A glove for covering a portion of a mammalian body wherein the glove, when exposed to light and/or moisture, is capable of reducing odor and/or microbiological contamination on the portion of the body and reducing odor and/or contamination of a surface in contact with the glove, wherein the glove comprises a gas releasing monolayer, the gas releasing monolayer prepared from a composition comprising:
   from about 74% to about 99% by weight of a plastisol comprising PVC resin and a plasticizer;

from about 0.005% to about 3% by weight of a thixotropic agent;

from about 0.01% to about 3% by weight of a dispersing agent; and from about 0.5% to about 20% by weight of a gas-generating composition which is capable of generating and releasing at least one gas selected from chlorine dioxide, chlorine, sulfur dioxide, carbon dioxide and/or nitrous oxide, the gas being released from the glove upon exposure of a surface of the glove to light and/or humidity.

8. A method of using a gas-releasing body covering article to reduce microbiological contamination and/or odor, the method comprising:

contacting a portion of a mammalian body with a body covering article;

exposing the body covering article to light and/or humidity to generate at least one gas, the body covering article comprising a gas releasing monolayer prepared from a composition comprising from about 74% to about 99% by weight of a plastisol comprising PVC resin and a plasticizer, from about 0.005% to about 3% by weight of a thixotropic agent, from about 0.1% to about 3% by weight of a dispersing agent, from about 0.5% to about 20% by weight anions which are capable of generating and releasing the at least one gas selected from chlorine dioxide, chlorine, sulfur dioxide, carbon dioxide and/or nitrous oxide, and a colorant capable of changing color when oxidized by the gas; and monitoring the color change of the colorant as an indicator of gas-releasing activity.

9. The method of claim 8 wherein the composition is capable of generating and releasing at least one gas upon exposure to light.

10. The method of claim 8 wherein the covering and/or body is contaminated with a microbe and the contamination and/or odor is reduced in less than five minutes after the exposure to light or moisture.

11. The method of claim 10 wherein the covering and/or body is contaminated with a microbe and the contamination and/or odor is reduced in less than one minute after the exposure to light or moisture.

12. The method of claim 8 wherein the covering and/or body is contaminated with a microbe and at least 50% of the microbial contamination is reduced in less than one minute after the exposure to light or moisture.

13. The method of claim 12 wherein the covering and/or body is contaminated with a microbe and at least 80% of the microbial contamination is reduced in less than one minute after the exposure to light or moisture.

14. The method of claim 13 wherein the covering and/or body is contaminated with a microbe and at least 90% of the microbial contamination is reduced in less than one minute after the exposure to light or moisture.

15. The method of claim 8 wherein the contamination and/or odor is reduced on an exterior surface of the covering and on an interior surface of the covering in contact with the portion of the body.

16. The method of claim 15 wherein the covering is a glove and the portion of the body is a human hand and the glove covers the hand, wherein the contamination and/or odor is reduced on the interior surface of a glove in contact with skin on a hand.

* * * * *